(12) United States Patent
Hlavinka et al.

(10) Patent No.: US 7,582,049 B2
(45) Date of Patent: Sep. 1, 2009

(54) FLUID SEPARATION DEVICES, SYSTEMS AND/OR METHODS USING A CENTRIFUGE AND ROLLER PUMP

(75) Inventors: Dennis J. Hlavinka, Arvada, CO (US); William G Palsulich, Lakewood, CO (US); Thomas J. Felt, Boulder, CO (US); Frank Corbin, III, Littleton, CO (US)

(73) Assignee: CaridianBCT, Inc., Lakewood, CO (US)

( * ) Notice: Subject to any disclaimer, the term of this patent is extended or adjusted under 35 U.S.C. 154(b) by 662 days.

(21) Appl. No.: 11/307,451

(22) Filed: Feb. 8, 2006

(65) Prior Publication Data

US 2006/0122048 A1 Jun. 8, 2006

Related U.S. Application Data

(63) Continuation of application No. 10/413,890, filed on Apr. 14, 2003, now Pat. No. 7,033,512.

(60) Provisional application No. 60/372,574, filed on Apr. 12, 2002.

(51) Int. Cl.
*B04B 5/02* (2006.01)

(52) U.S. Cl. ................ 494/16; 417/475; 417/477.1; 494/31; 494/33; 494/56

(58) Field of Classification Search ........... 210/87, 210/97, 512.1; 422/72; 494/1, 7, 10, 16–18, 494/21, 31, 41, 43, 44, 50–52, 56, 57, 60, 494/84, 85, 33; 417/475, 476, 477.1

See application file for complete search history.

(56) References Cited

U.S. PATENT DOCUMENTS 3,211,368 A 10/1965 Shanley (Continued)

FOREIGN PATENT DOCUMENTS

EP 0587257 6/1998

(Continued)

OTHER PUBLICATIONS

International Search Report for corresponding application PCT/US03/11624.

*Primary Examiner*—Joseph W Drodge
(74) *Attorney, Agent, or Firm*—Edna M. O'Connor; John R. Merkling; Laura B. Arciniegas

(57) ABSTRACT

A centrifugal fluid separation system is disclosed for centrifugally separating a composite fluid into components thereof. This centrifugal separation system includes at least a centrifugal rotor which has a composite fluid containment area, a fluid flow channel/tubing and at least one separated component collection area defined therein. A composite fluid to be separated is delivered to the fluid containment area where under centrifugal forces the composite fluid is separated into components and then from which a component travels through an outlet channel to a respective separated component fluids flowing therethrough. A centrally disposed pump is also provided to move the separated component(s) to the collection area(s). Optical sensing of the interface of the separated fluid components may be used with a clamp to stop flow. A disposable bag and tubing system is also disclosed for use with reusable rotor devices.

24 Claims, 15 Drawing Sheets

U.S. PATENT DOCUMENTS

| | | | |
|---|---|---|---|
| 3,559,880 A | 2/1971 | Naito et al. | |
| 3,724,747 A | * 4/1973 | Unger et al. | 494/1 |
| 3,761,014 A | 9/1973 | Carter | |
| 3,901,658 A | * 8/1975 | Burtis et al. | 422/104 |
| 4,113,173 A | 9/1978 | Lolachi | |
| 4,241,866 A | 12/1980 | Giesbert et al. | |
| 4,303,193 A | * 12/1981 | Latham, Jr. | 604/6.04 |
| 4,447,220 A | 5/1984 | Eberle | |
| 4,663,296 A | * 5/1987 | Revillet et al. | 436/45 |
| 4,738,655 A | 4/1988 | Brimhall et al. | |
| 4,850,952 A | 7/1989 | Figdor et al. | |
| 4,963,498 A | * 10/1990 | Hillman et al. | 436/69 |
| 5,525,218 A | 6/1996 | Williamson et al. | |
| 5,653,887 A | * 8/1997 | Wahl et al. | 210/745 |
| 5,720,716 A | 2/1998 | Blakeslee et al. | |
| 6,011,490 A | 1/2000 | Tonnesen et al. | |
| 6,325,750 B1 | 12/2001 | Jorgensen et al. | |
| 6,413,200 B1 | 7/2002 | Jorgensen et al. | |
| 6,495,351 B2 | * 12/2002 | McHale | 435/173.6 |
| 6,802,804 B1 | 10/2004 | Stroucken | |
| 2002/0046967 A1 | 4/2002 | Romanauskas et al. | |

FOREIGN PATENT DOCUMENTS

| | | |
|---|---|---|
| WO | WO92/00145 | 1/1992 |
| WO | WO01/97943 | 12/2001 |

* cited by examiner

FLUID SEPARATION DEVICES, SYSTEMS AND/OR METHODS USING A CENTRIFUGE AND ROLLER PUMP

RELATED APPLICATIONS

This case is a continuation of U.S. patent application Ser. No. 10/413,890 filed Apr. 14, 2003, now U.S. Pat. No. 7,033,512, which claims the benefit of priority of U.S. Provisional Patent Application Ser. No. 60/372,574 filed Apr. 12, 2002.

INTRODUCTION

The present invention is directed generally to centrifugal fluid separation devices and more particularly includes a roller pump driven configuration usable with one or more disposable tubing and bag sets.

BACKGROUND OF INVENTION

In the United States, millions of units of donated whole blood are collected by blood banks each year. Whole blood is made up of red blood cells, white blood cells (also called leukocytes), and platelets, all suspended in a protein-containing fluid called plasma. Because patients are not likely to require each component of whole blood, most of the whole blood collected from donors is not stored and used for transfusion. Instead, the whole blood is separated into its clinically therapeutic components, red blood cells, platelets and plasma. The components are stored individually and used to treat a multiplicity of specific conditions.

A number of fluid separation devices have been known and various models are currently available for the separation of whole blood or other composite fluids into the various component elements thereof. For example, a variety of centrifugal machines are available for separating blood into component elements such as red blood cells, platelets and plasma, inter alia.

Centrifugation in the past has been used for separation in many forms in both continuous and batch types. For example, in the widely used process known as continuous centrifugation, as generally opposed to batch process centrifugation, a continuous input of a composite fluid is flowed into the separation device or chamber while at the same time the components of that composite fluid are substantially continuously separated and these continuously separating components are usually then also substantially continuously removed therefrom. Many currently popular forms of such continuous fluid separation devices include loops of entry and exit flow tubing lines connected to the separation centrifuge chamber such that each loop is rotated in a relative one-omega-two-omega (1ω-2ω) relationship to the centrifuge chamber itself so that the tubing lines will remain free from twisting about themselves.

An alternative form of tubing line connection to a continuous centrifugal separation device is also available in the art which does not have such a loop, but which instead requires one or more rotating seals at the respective connections of the tubing lines to the centrifuge separation chamber, again to maintain the tubing lines free from twisting.

Batch-type centrifugation, on the other hand, usually involves separation of a composite fluid such as whole blood in a closed container, often a deformable bag, followed by removal of the container/bag from the separation device and then subjecting the container/bag to a relatively difficult process of automated and/or manual expression of one or more of the separated components out of the separation container or bag. A great deal of control, either automated, such as by optical interface detection, or by a diligent human operator watching a moving interface, is required with such previous batch-type processes.

One type of known batch-type centrifuge uses buckets for holding bags of, for example, whole blood collected from a donor. The buckets rotate to separate the components inside the bags. The bags are then removed from the centrifuge where they are expressed by an operator using a manual expressor to remove components from the bag. Another type of centrifugal apparatus that also functions as a cell washer is the COBE 2991 system available from Gambro BCT, Inc., Lakewood, Colo. The COBE 2991 as well as PCT International Publication No. WO01/97943 and U.S. Pat. No. 6,315,706 use an expressor fluid or hydraulic fluid for removing separated components.

Indeed, various means and methods have been used in or with prior centrifugal separation systems, both continuous and batch, for driving fluid flow and maintaining desirable interface position control between the component elements being separated thereby. For example, as mentioned, various optical feedback methods and devices have been employed in the art. Various pumping and valving arrangements have also been used in various of these and other arrangements. Alternative relatively automatic volume flow and density relationship interface controls have also been used; for example, in a continuous system by the disposition of control outlet ports in strategic locations relative to the separated component outlet ports.

Nevertheless, many facets of these prior separation devices, though providing heretofore satisfactory production, may yield certain features which are less efficient than a desired optimum. For example, for collecting random donor platelets from whole blood it was necessary to have a second spin and tighter control over the interface between components which in the past was difficult with a manual expressor. Another disadvantage of prior art systems is that frequently the interface was required to move. For example, in hand or manual expression, the interface moves during the component removal process. This can result in difficulties in maintaining the desired interface for optimum collection.

Hence, substantial desiderata remain to provide a more highly efficient centrifugal separation device particularly for whole blood in terms of increased efficiency fluid flow drive and separation interface controls; and/or reduced seal need and/or intricacy. It is toward any one or more of these or other goals as may be apparent throughout this specification that the present invention is directed.

BRIEF SUMMARY OF THE INVENTION

The present invention is directed generally to centrifugal fluid separation devices and/or systems for use in centrifugally separating whole blood or composite fluids into the component elements thereof. Such centrifugal separation systems include centrifugal rotor and rotor/fluid container combinations in which each rotor with one or a plurality of containers positioned therein, may together be disposed in a flow control disposition relative to a roller pump assembly. The roller pump assembly may be concentric with and/or disposed on/in the rotor and is adapted to engage one or more tubing lines of one or more tubing and bag sets as these may be disposed on/in the rotor. One or more totally closed systems may thus be provided hereby. Also provided are simple sterilization and disposability of the fluid container/tubing combination(s) as well as simple loopless and rotating seall-ess rotors for composite fluid (e.g., whole blood) separation.

Each rotor has one or more buckets or like fluid receiving/containing areas and at least one corresponding fluid roller pump head and race associated therewith. Provision is also made for fluid flow from the containment area to and through the pump head/race and then back to the same or a discrete fluid containment/receiving area. Such provision may be made by a flow channel and/or a tubing line, the tubing line being either discrete from or part of a closed fluid container and tubing set. In one embodiment, a composite fluid to be separated into component parts may then be delivered to the fluid receiving or containment area in a composite fluid container or bag. Then, when subjected to centrifugal forces, the composite fluid may be separated into respective components while residing in the respective initial fluid containment area. These components may be halted from leaving the containment area by action of a flow blocking mechanism or clamp or by occlusion by a roller pump head against the tubing line, the roller pump head remaining motionless relative to the tubing line and thus maintaining the occlusion of the tubing line. Then, once the components (e.g., plasma and red blood cells or other components, inter alia) of the composite fluid have been appropriately and/or desirably separated, a first one (usually the lighter) of these components may be pumped while the centrifuge continues to rotate so as to travel through respective channel tubing lines to the respective component collection areas where they may be collected in respective collection containers or bags. Each such collection container may be disposed in the same initial fluid containment area or a discrete receiving area on or as connected to the rotor. A clamping closure of the tubing line may then be effected and the centrifuge stopped. These separated fluids may then be removed from the separation device in or from the container(s), or deformable bag(s). After removal from the centrifuge, they may be stored, further processed, or may be transfused into a patient. The composite fluid in this process may be whole blood, and the respective components may then be plasma and red blood cells (RBCs), although buffy coats and/or platelets, inter alia, may also be harvested herewith. Alternatively, the composite fluid can be previously collected blood or blood components for further separation. Other blood processing operations, such as component washing, or the addition of plasma may also be performed herewith. Also, RBC deglycerolization or pathogen reduction or agent removal may be performed.

For a composite fluid such as whole blood, where the respective densities of the separable component parts, e.g., plasma and RBCs, are known (within sufficiently controllable ranges), then appropriate collection containers or bags and pumping systems can be chosen. After separating, the interface is held substantially in position by the centrifugal field as the plasma is pumped during the pumping/flow process. As the bag or container collapses from the top down the interface substantially remains in position. An optical sensor may be established at or adjacent to one or more tubing lines such that as soon as a discrete colored or varied substance (e.g., RBCs relative to plasma) reaches the optical sensor by flowing to tubing after plasma collection the sensor can signal the need to stop flow. The signal can provide for effecting a clamping of the tubing line on the suction side of the pump to avoid overpressure of the tubing and to conclude the separation. Similarly, if another type of monitor is used, this monitor can signal for any desired clamping or automatically stop flow. This pumping relationship governs a general forcing of the fluid flow in one direction out of the initial receiving/containment area, into the separation channel/tubing line and from there into the respective component collection areas which again could be the same as the initial containment areas.

The instant invention has the advantage that although the plasma amount of the starting product or composite fluid may vary, the proper separation can be achieved. That is, the completion of the process is determined by the identification of a discrete colored substance, for example RBCs, or the heavier or more dense substance reaching the sensor.

It is to be understood that both the foregoing general description and the following detailed description are exemplary, and are intended merely to provide limited explanation of preferred embodiments of the invention as more broadly claimed. These and further aspects of the present invention will become clearer from the detailed description read in concert with the drawings in which like component elements are referenced therein with like component numbers throughout the several views.

DESCRIPTION OF A DETAILED EMBODIMENT

FIGS. 1-16 are used to describe the embodiments below. Such figures and the elements thereof are representational only and are not necessarily to scale.

A fluid separation system according to the present invention is depicted in the attached drawings and identified by the general reference number 10 therein. Note, the processing of whole blood as the composite fluid is described in the embodiments herein, although other composite fluids with or without certain blood components may also be processed hereby. Red blood cells (RBCs) and plasma are the primary components described as separated from whole blood herein, although processing for the separation and collection of buffy coats, platelets or white blood cells, inter alia, may also be accomplished herewith. Blood component processing such as in washing, adding plasma, or removing additive materials may also be performed as described here. RBC deglycerolization or the removal of a pathogen reduction agent from an RBC or platelet component product may also be accomplished herewith as described below. With a few sequence modifications, the primary process generally is also applicable to facilitate wash and/or removal from a blood component of any supernatant such as a pathogen reduction agent solution (e.g., photosensitizers such as psoralens, methylene blue, and/or the like) from RBCs or other components (e.g., platelets) undergoing a pathogen reduction process. This could occur in substantially the same fashion as removing the plasma from the other component(s). RBC, plasma, and/or platelet collections from whole blood may provide a further option which, in one embodiment, could provide customers with all three products following a single spin of whole blood, packed RBCs in one bag, pelletized platelets or buffy coat platelets in a second bag, and plasma in a third bag. An example of sequencing to yield the three products following a single spin will be set forth below.

Figure 1:
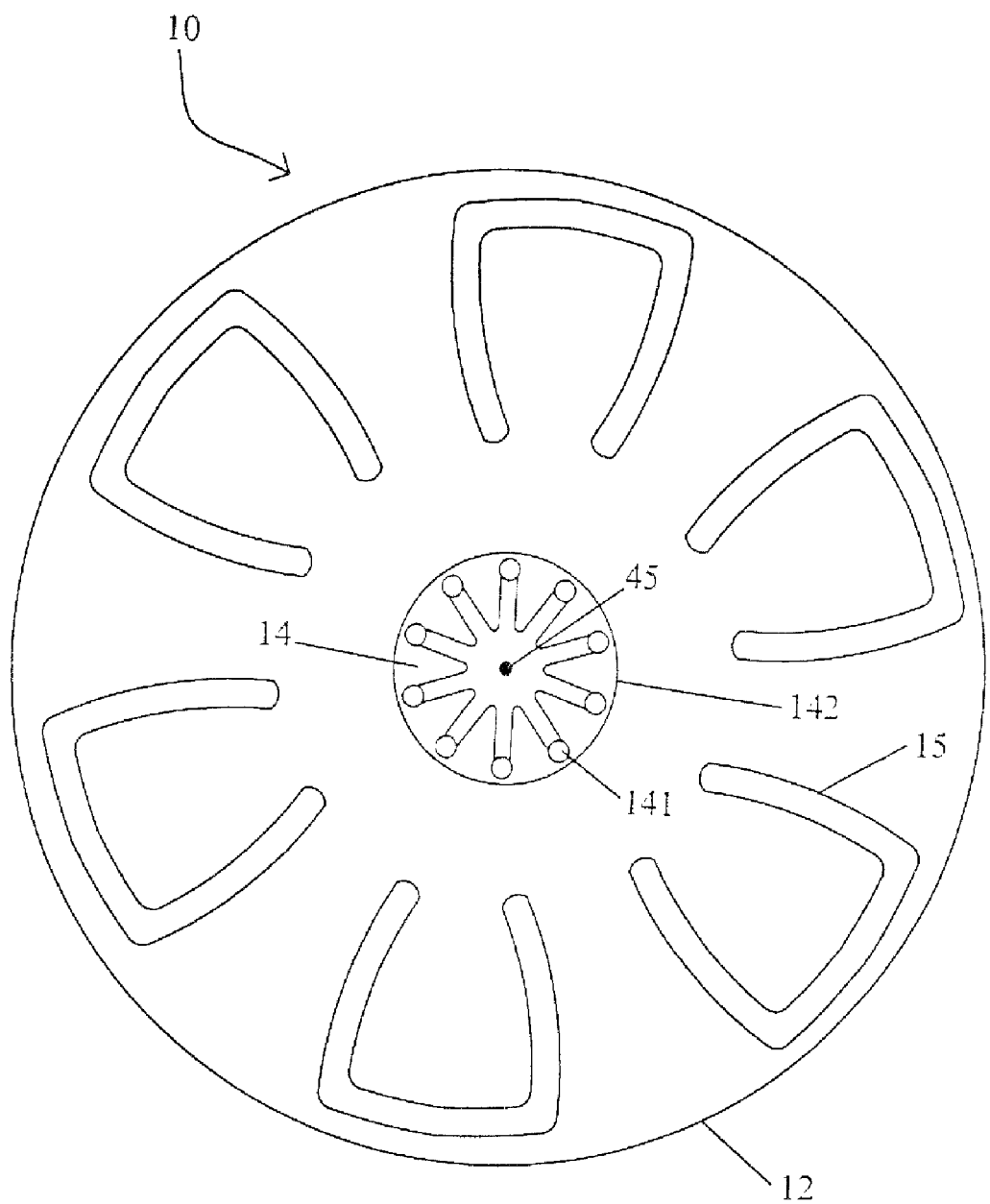
FIG. 1 is a plan schematic view of a rotor according to the present invention.
Figure 2:
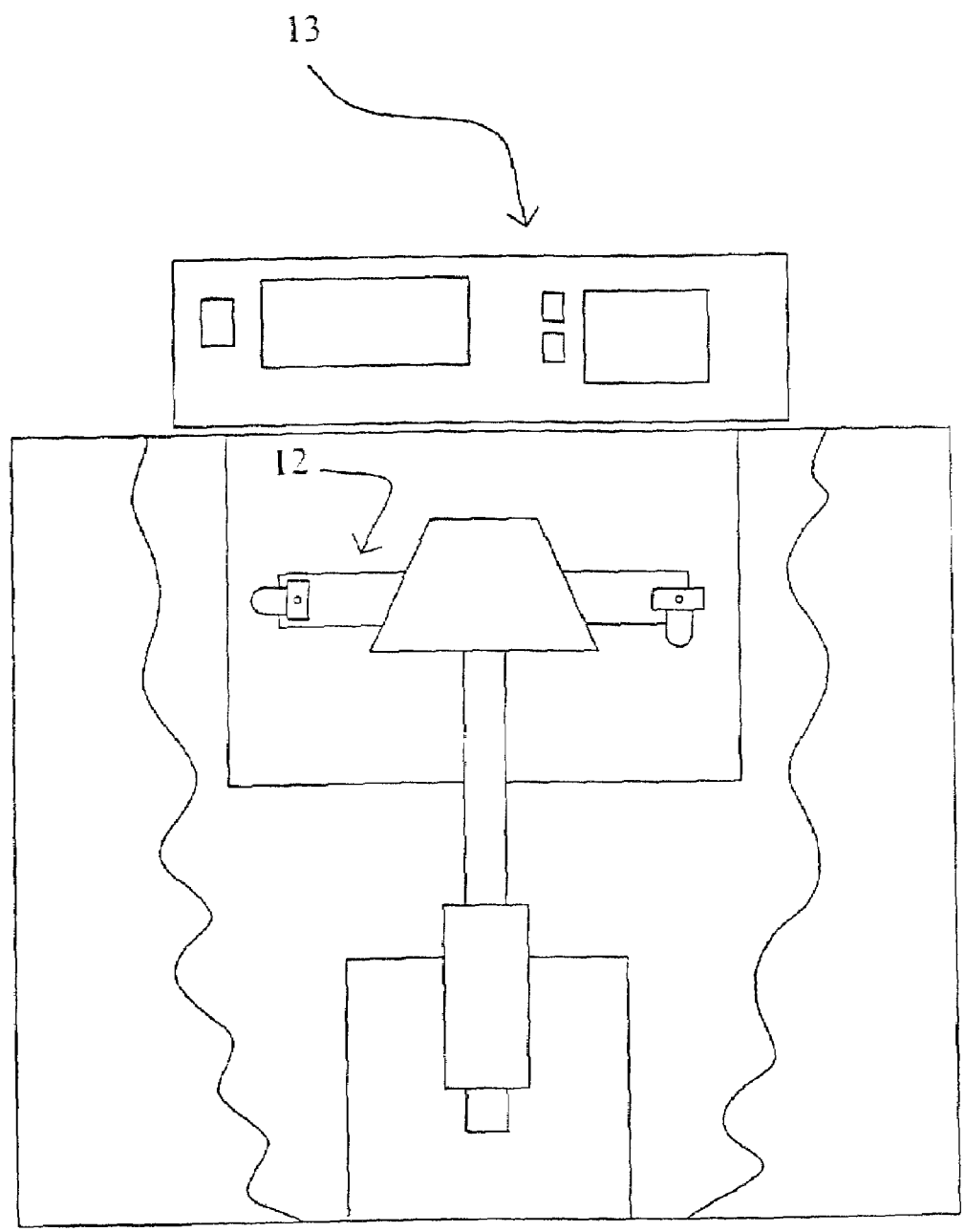
FIG. 2 is a schematic view of a centrifuge according to the present invention.

As shown in a first embodiment, for example in FIG. 1, a separation system 10 may generally include a rotor 12 (shown schematically) with a pump arrangement 14. These may be used in a possibly unique or perhaps even in a conventional centrifuge 13 (see FIG. 2). Although generally in a conventional centrifuge the buckets or containment areas pivot during centrifugation, such a feature is not necessary with respect to the present invention. That is, the buckets or containment areas can be fixedly mounted on the rotor. The rotor 12 may also include one or more containment areas or buckets 15 (six shown). A bag and tubing system 16, see FIG. 3, may be used herewith as shown for example in FIGS. 5-8 where each such tubing set 16 has one or more respective tubing line(s), only one such respective line 18 being shown in FIGS. 4-8 (access needle tubing line 17 (FIG. 3) having been removed), and associated reservoirs or bags 20, 22. As introduced, a tubing set 16 with associated tubing line(s) or conduit(s) or transport channels 18, and bags 20, 22 is shown in more detail in FIG. 3 and is further described below. These primary component parts and some optional tubing lines and associated optional componentry will also be further described below. Note, the option of using an anticoagulant (A/C), though such anticoagulant may and often will be pre-packaged (not directly shown) in the whole blood collection bag 20, and/or may be later added (after disconnection from the donor).

It is understood that other features found in disposable tubing sets can be used with the principles of the current invention. For example, filters for leukoreduction or other purposes and/or containers including storage solution or other additive solutions may be included in the desired disposable.

FIGS. 1 and 5-8 show a six bucket centrifuge rotor 12 with a roller pump mechanism 14 located concentrically with the centrifuge rotor 12. The pump heads 141 are free to rotate relative to the rotor 12 around axis 45. The race 142 is fixed to the rotor 12 and must therefore rotate at the same rate as the rotor 12. Whole blood bags 20 and plasma bags 22 are placed into the buckets 15 as shown in FIGS. 5-8. The tubing lines 18 connecting the two bags 20, 22 of the respective sets 16 (see FIG. 3) are loaded into a channel including the roller pump raceways 142 (see FIG. 4). Note, all or part of tubing lines 18 may be of sufficient strength and/or thickness to be adapted to operate in a pump raceway, or alternatively a tubing header portion (possibly thicker or of slightly different material) may be appropriately formed or otherwise disposed in tubing line 18 in adaptation for operable engagement with the pump 14.

Figure 4:
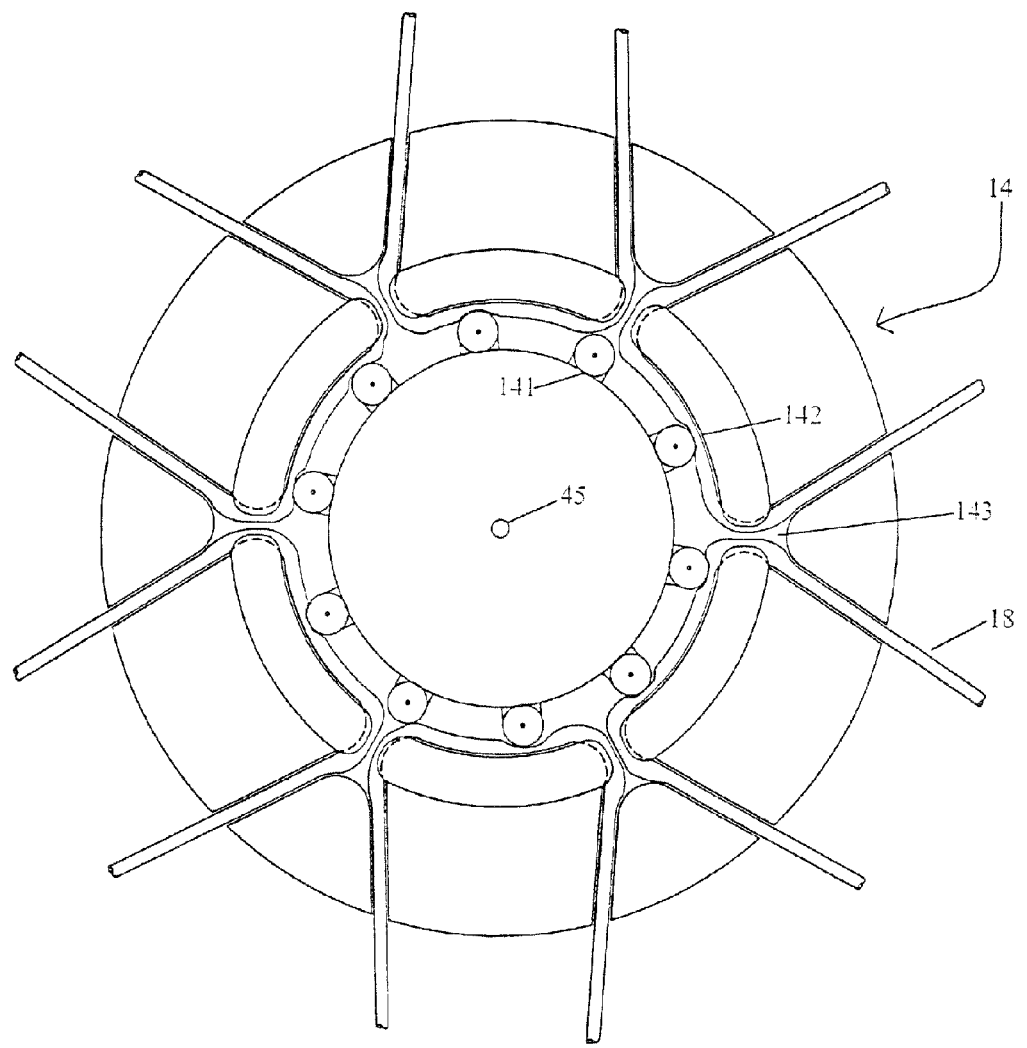
FIG. 4 is a portional plan view of a rotor with tubing according to the present invention.

FIG. 4 also shows an enlarged depiction of one possible embodiment of a raceway system engagement with one tubing segments 18. The raceway walls 142 against which the heads 141 roll and compress respective tubings 18 are shown. Additional slots 143 are also shown for accommodating tubings 18 in this embodiment. As shown there is at least one conduit engaging head 141 associated at any one time with each piece of tubing 18 so that the tubing may be occluded. The number of conduit engagement heads 141 in the pump assembly 14 can be varied and are selected so that there is at least one head 141 associated at any one time with each tubing 18.

Figure 5:
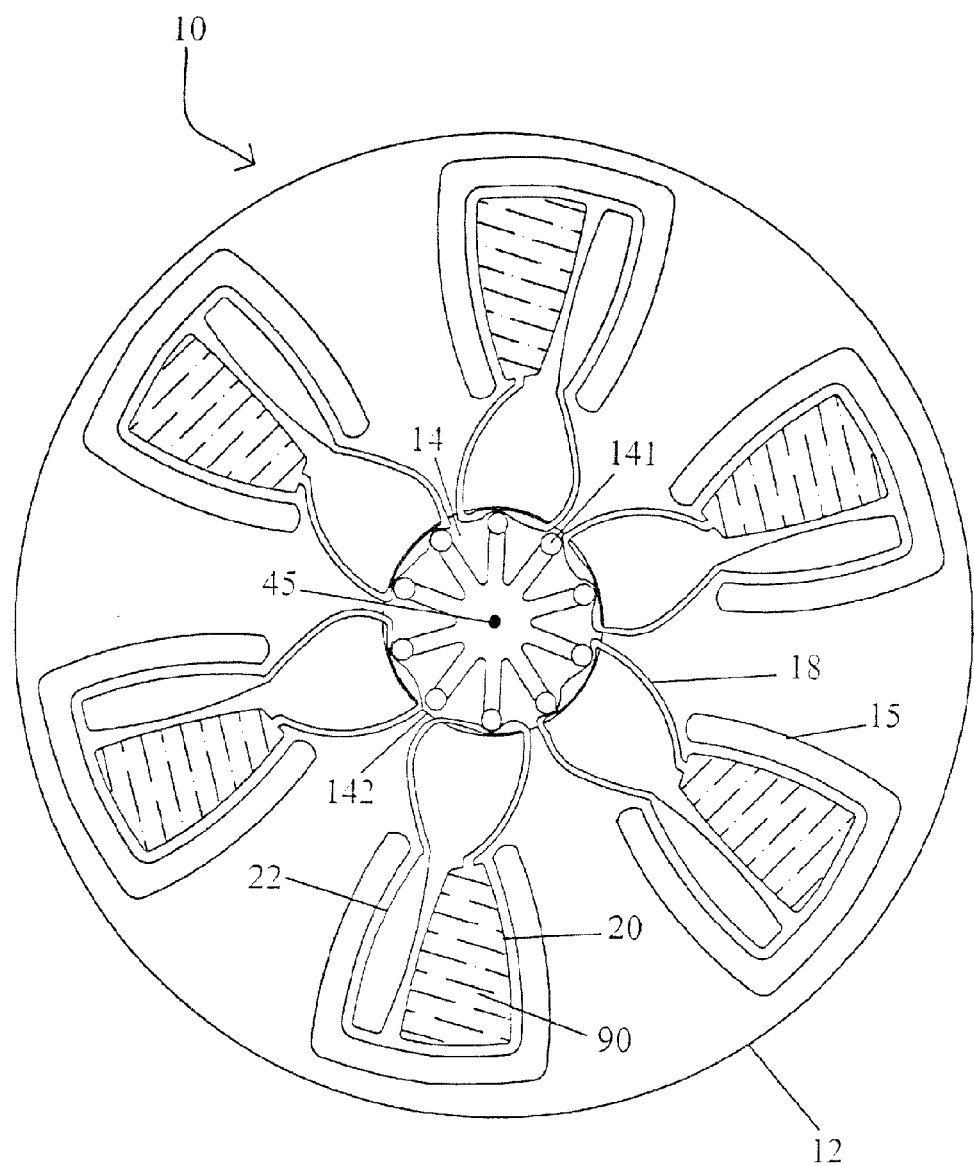
FIG. 5 is a plan view of a rotor such as that shown in FIG. 1 including therein a tubing and bag system like that shown in FIG. 3.
Figure 6:
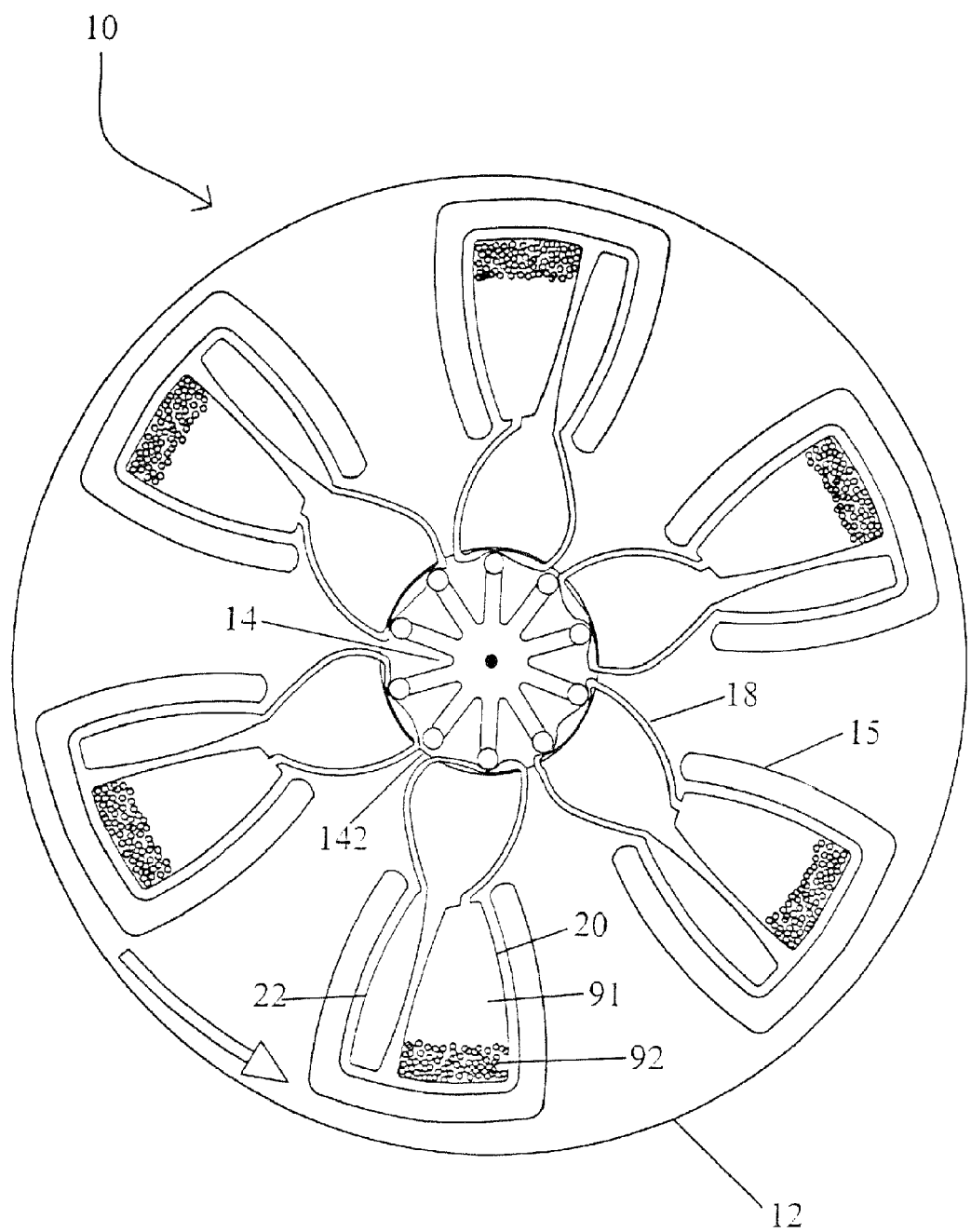
FIG. 6 is a plan view of the rotor of FIG. 5 after separation.
Figure 7:
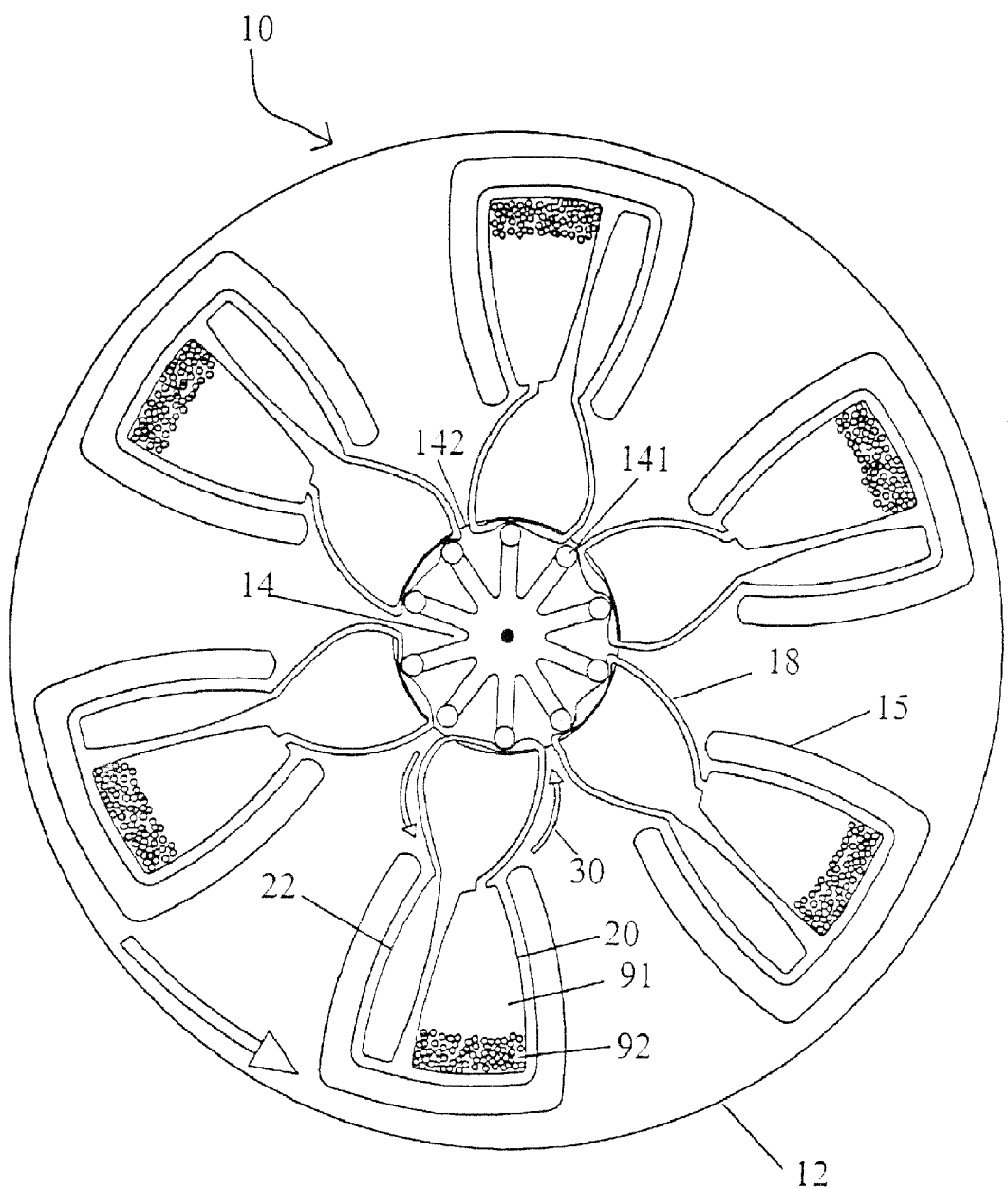
FIG. 7 is a plan view of the rotor of FIG. 5 during pumping.

FIG. 5 shows the centrifuge as loaded and prior to actual separation of components with whole blood in bags or containers 20 inside the container area or buckets 15. FIG. 6 shows the rotor 12 spinning at high RPM in the counter clockwise direction. Due to friction between each pump head 141 and each tubing line 18 loaded in each race 142, the pump head 141 will rotate with and at the same RPM as the race/rotor combination and therefore fluids will not be pumped. At this high RPM, RBCs 92 and plasma 91 will separate in each respective bag 20. FIG. 7 shows a subsequent period after that shown in FIG. 6 with the rotor 12 reduced to a low RPM maintaining rotation of the rotor 12 and the race 142. A mechanism 201 (not shown in FIG. 7 but see FIG. 15) is used to stop rotation of the pump head assembly 14 resulting in relative motion between the still rotating rotor 12 and pump race 142 and the pump head assembly 14. Alternatively, the relative motion between the pump assembly 14 and the pump race 142 can be achieved by varying the speed or RPMs of one of the pump assembly 14 or the pump race 142 as compared to the other. Also, the rotor 12 and pump race 142 can be stopped while the pump assembly 14 is rotated. Again the only limiting feature is that there be relative movement between the pump assembly 14 and the pump race 142 to produce the pumping motion. This relative motion results in a pumping action with plasma being pumped into the plasma bag 22.

Figure 8:
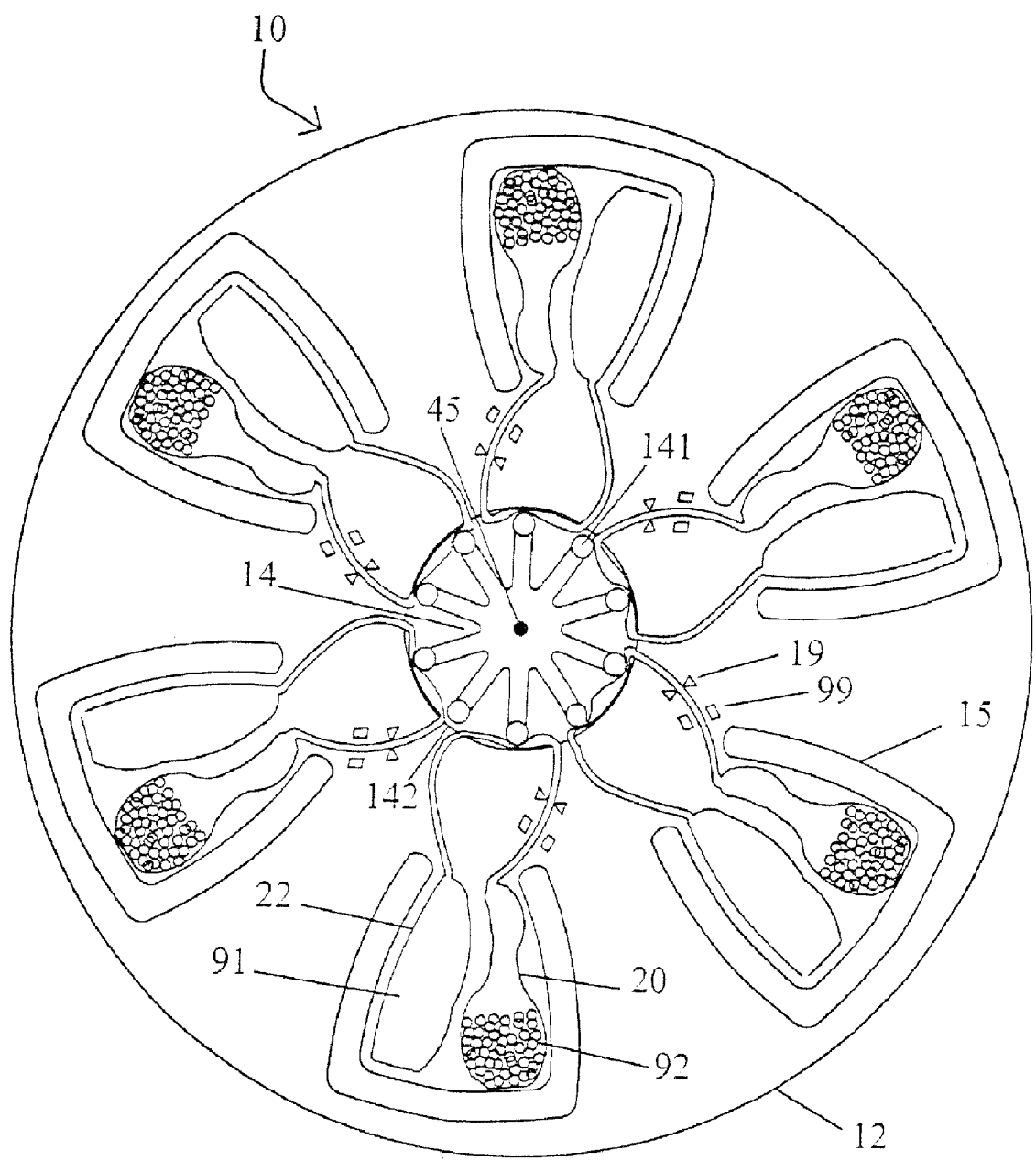
FIG. 8 is a plan view of the rotor of FIG. 5 with clamping.

Optical or other sensors 99 (not shown in FIGS. 5 and 6, see below and FIG. 8) may be used to sense the presence of RBCs 92 in each tube 18 and trigger clamps 19 for each bag preventing the transfer of red blood cells 92 to plasma bag 22. This also permits variable volumes of plasma 91 to be pumped into each bag 22. FIG. 8 depicts each tubing 18 clamped on the suction side of the pump head 141, thus preventing overpressure of each tubing 18 as rotation of the rotor continues.

Figure 9:
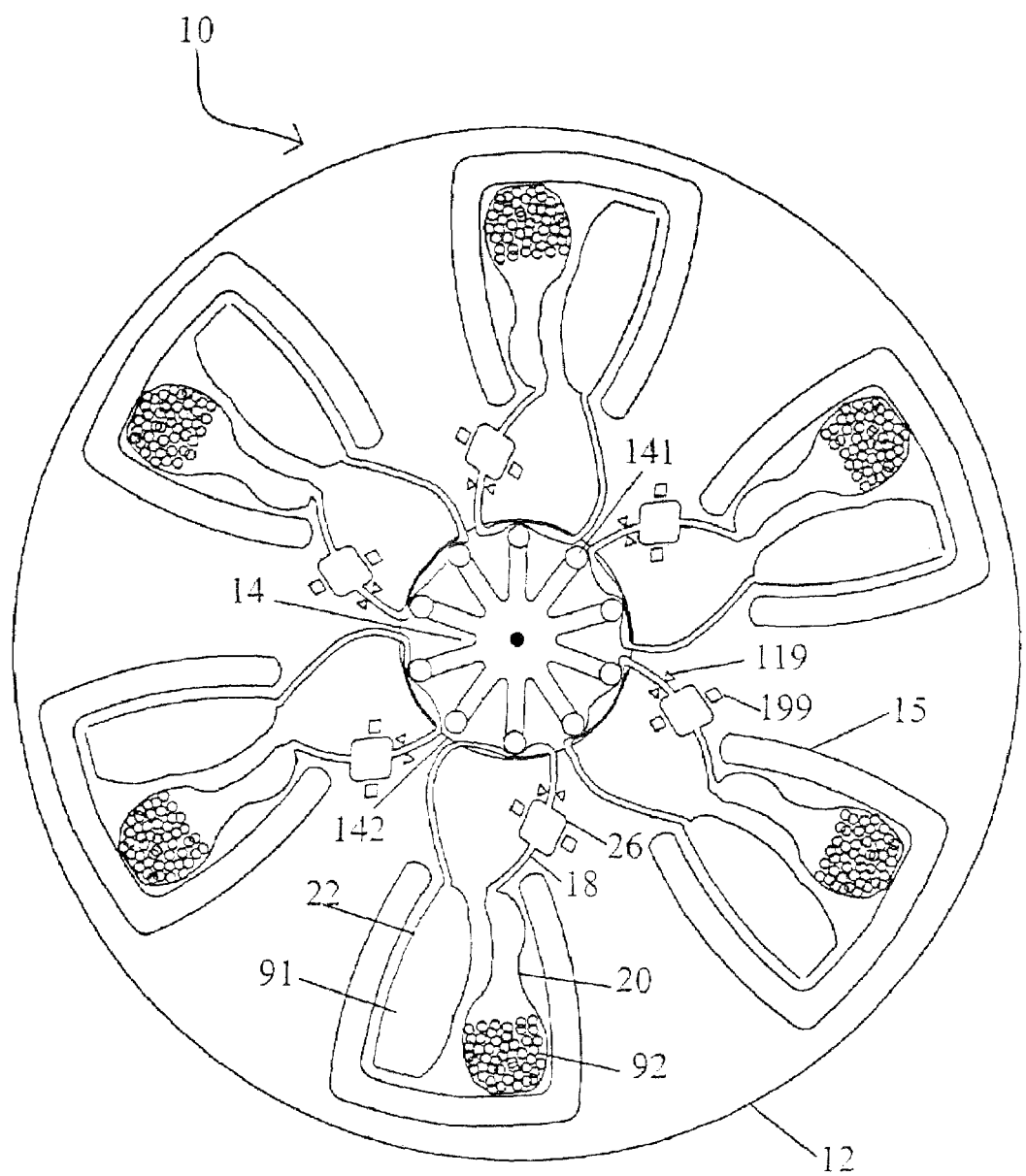
FIG. 9 is a plan view of a rotor such as those shown in FIGS. 5-8 with an alternative bag and tubing set.
Figure 10:
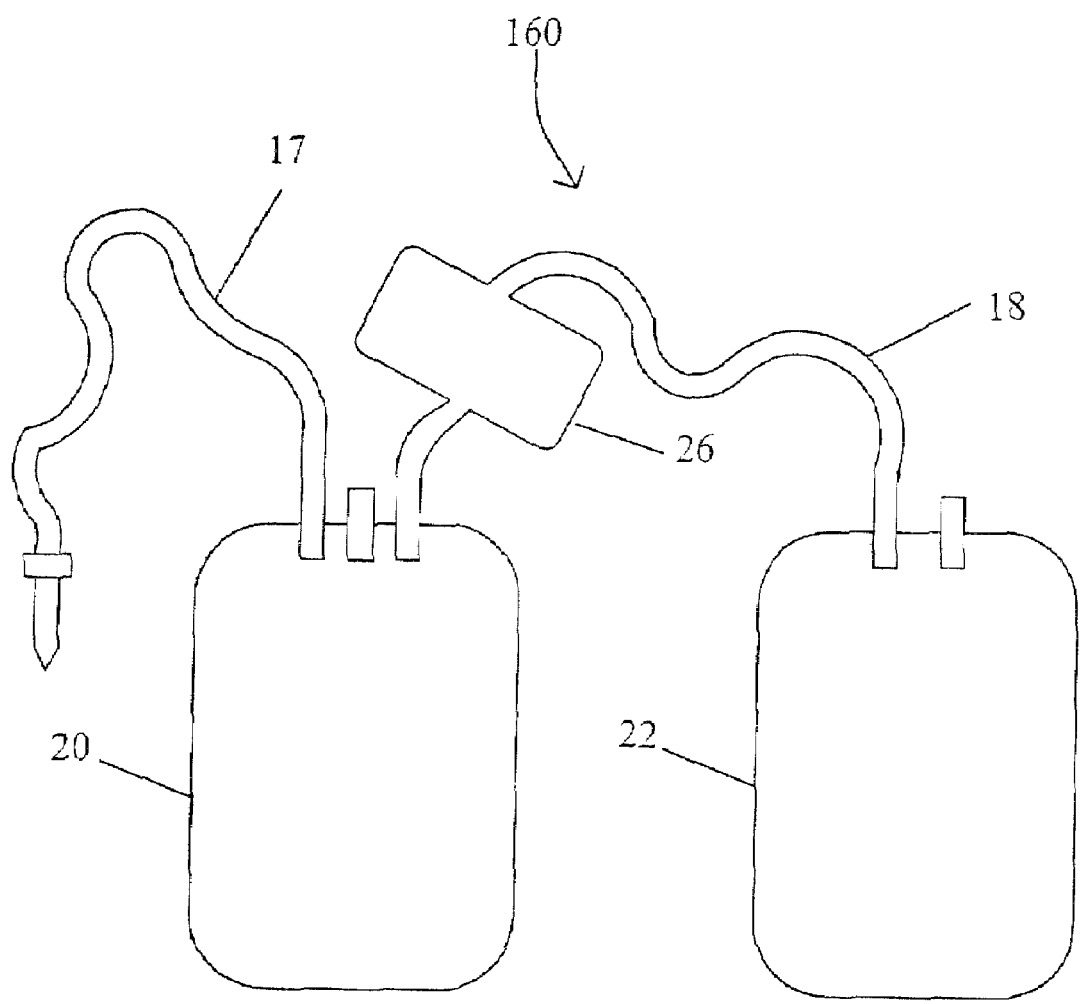
FIG. 10 is a view of a first alternative bag and tubing set such as that shown in FIG. 9.

FIGS. 9 and 10 show an alternative bag set 160 (FIG. 10) having an additional container or bag 26 in the tubing line 18 to collect platelet containing buffy coats. Again, clamp sensors 199 can be used to monitor the passage of components wherein red blood cells in general remain in bag 20, buffy coats in bag 26 and plasma moves to bag 22. FIG. 10 shows bag set 160 apart from the rotor 12. If bag 26 is placed into a rigid, constant volume chamber or container on/in rotor 12, (see FIG. 9) all buffy coat collections will contain the same volume of buffy coat product. As noted above, the use of rigid containers is a possible alternative for all bags.

As shown in FIG. 1 and also in FIGS. 5-8, a rotor 12 may have six (or more or less) general containment areas or buckets 15 (also sometimes referred to as pockets herein). These areas 15 may be where the composite fluid (e.g., whole blood) is received and initially contained, then also where the separation is accomplished. Thus, these areas may be referred to as containment and/or separation and/or containment/separation areas. These same areas 15 may also be where RBCs are retained and/or collected in a storage container which may be discrete from or identically the same as bag 20 and may also include a plasma collection area or bag 22 for collection of plasma. These buckets or areas 15 may include all of these sub-areas with or without specifically bounded means 183, i.e., walls or partitions (not shown in FIG. 1, but see FIG. 11) inside the buckets or areas 15 to subdivide each bucket or area 15 into respective separated component sub-areas 184, 185, e.g., an RBC sub-area and a plasma sub-area (see FIG. 11). Such partitions or walls may optionally be moveable in some fashion to allow for re-distribution of separated material from a configuration such as that shown in FIGS. 3-5 (where all materials, separated or otherwise) reside in a single container 20, to the configuration shown in FIG. 8 where a certain quantity of separated materials have been moved from the first container 20 to the second container 22. As shown in FIG. 8 this resulting relationship is side-by-side. However, the relationship could instead be one on top of the other, or otherwise distributed, particularly if physical boundary members (e.g., walls or partitions) are used. Also, optionally, the plasma container or bag could be a closer radial distance than the whole blood or other container bags although this is optional and not necessary.

As depicted in FIG. 6, the separation is effected by rotation in the counterclockwise direction at high RPMs in an overall fluid flow configuration presented by rotor 12 and pump assembly 14 which rotate together to provide a no-flow situation at high RPMs. At a lower RPM forward flow control is provided by the heads 141, see FIG. 7. Then, the rotor configuration which includes a substantially central composite fluid pumping arrangement 14 which acts on transport channels or tubing 18 may be activated optionally at low RPMs by disengagement from the rotor (see element 201, FIG. 15) after separation completion. A transport channel may be discrete from or may solely include tubing 18, but provides for fluid communication from bag/container 20 to bag/container 22. Activation of the pumping action of the pump head assembly 14 at low RPMs may include a relative stoppage of pump head assembly 14 to zero (0) RPMs while the remainder of the rotor 12 continues to rotate at low RPMs or, alternatively, a relative change of speed can be used as described. When the pump head assembly is stopped the races 142 will continue to move relative to the stopped heads 141 which will then cause a peristaltic pumping action of fluid in tubing lines 18 from each bag 20 to each bag 22. The lighter phase component fluid which floats on top of the more dense phase will be first moved out of the bags 20 (see flow arrows 30 in FIG. 7). Pumping in this fashion may continue until the desired amount of component has been removed (see FIG. 8). As shown in FIG. 8 pumping of the lighter phase component 91 results in collapse of bag 20 from the top down leaving a relatively stable and stationary interface.

The above refers to separation by rotation in the counterclockwise direction followed by stoppage or changing speed of the pump assembly or pump race to produce relative movement between the pump assembly 41 and the pump race 142. It is understood, however, that the relative movement can be achieved in other ways as described above. It is further understood that the only limit on the direction of rotation for pumping (which could be in the clockwise direction), is that flow of the light phase component be toward the collection bag.

Visual monitoring by a human operator may be used to determine when flow should be halted; specifically, when substantially all (or a desired quantity) of the separated lighter phase component (e.g., plasma) is removed from bag 20 and moved to bag 22. Otherwise, a timing mechanism could be used to halt pumping or one or more optical sensors 99 (FIG. 8) or other sensors or level detectors as more fully described below could be used to sense when the heavier phase component (e.g. RBCs) begin leaving the bag 20, thus indicating when the lighter phase component has substantially been removed. Clamps 19 (shown schematically) or other flow stoppage members could then be activated on lines 18 (independently or simultaneously) when flow stoppage is desired (whether from visual, timing or optical or other types of sensing or detecting). Magnetic apparatus (not shown) to stop the relative movement between pump head assembly 14 and rotor 12 may be a means for this purpose. However, disc braking or other stopping means may also be available.

Other types of sensors and/or clamps or flow stopping devices could be used to prevent a heavier phase component from leaving bag 20. One such flow stopping device includes the use in the bag 20 of a ball of material of suitable density to float between the lighter phase and the heavier phase. Such a ball can effectively act as a plug for the bag 20 at the port leading to tubing 18, closing the entrance to tubing 18 when the red blood cells start to exit the bag.

Note, the rotor 12 shown in FIGS. 1 and 4-8 may be formed by various methods using a variety of materials. However, formed metals and/or molded plastics may also be used, as may other lightweight yet very durable parts. Simply designed pockets or containers 15 may then be easily constructed and disposed in rotor 12. The rotor 12 may be reusable with disposable bag and tubing sets, however the rotor 12 may also be made for disposability (as for example, if the rotor 12 may be used for blood separation without a bag set 16, e.g., formed channels and a fluid tight lid (not shown) may be disposed in/on rotor 12 which could thus be used for such a purpose). In either case, numerous repetitive uses with a series of discrete bag or container sets 16 may be used; such bag or container sets provide for the complete sealed enclosure of the blood and blood components therewithin so that the rotor 12 does not come into contact therewith. Rotor 12 would then require limited or no sterilization or disposal after each use.

Figure 14:
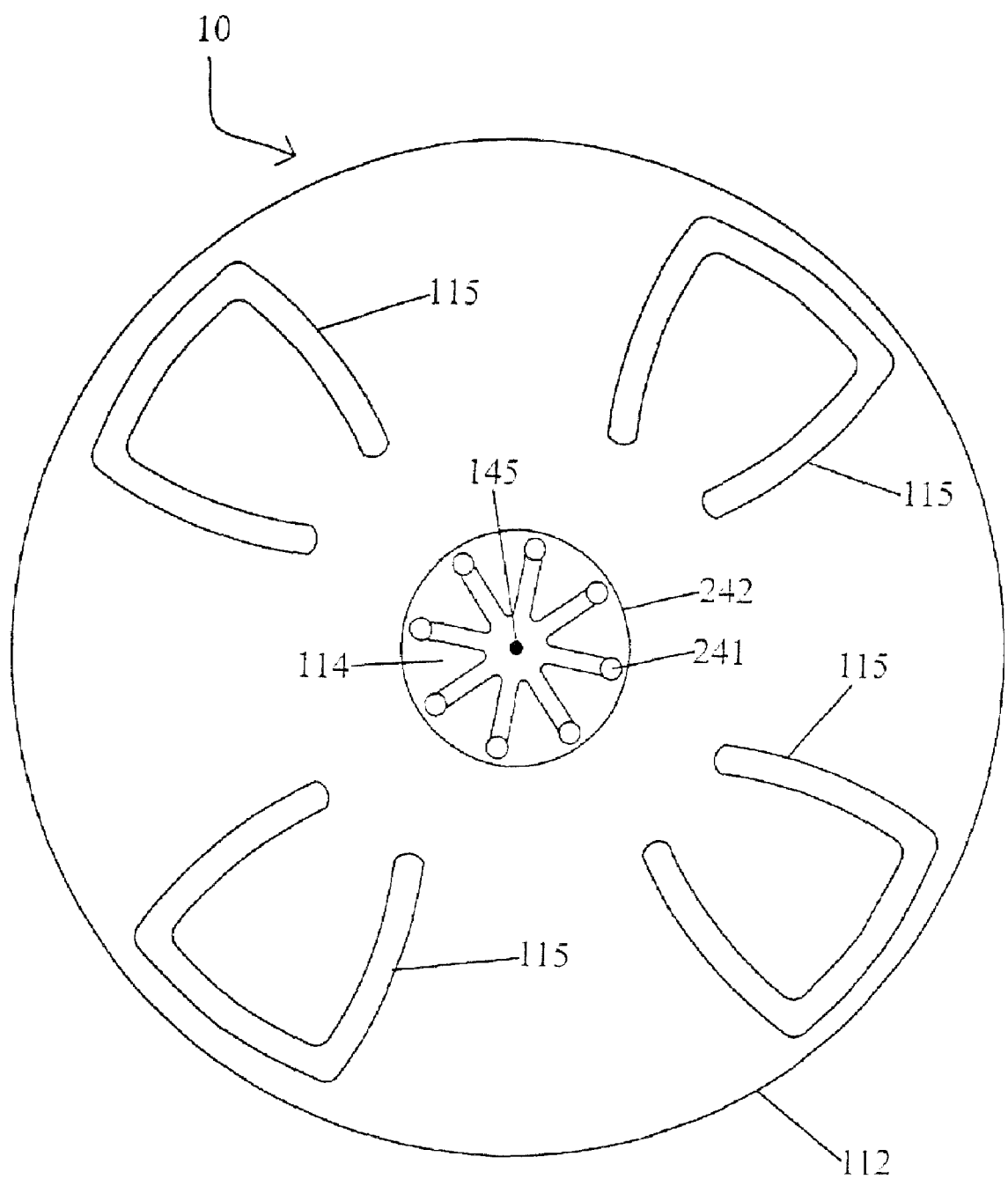
FIG. 14 is a plan view of a rotor alternative to accommodate four buckets in accordance with the instant invention.

An alternative rotor 112 having four containment areas or buckets 115 is shown in FIG. 14. This rotor 112 also has a substantially central composite pumping arrangement or assembly 114 with pump race 242 and axis 145. Pump heads 241 are arranged so that at any one time at least one pump head is adjacent tubing 18 (tubing not shown) of each bag set. Clamps or valves similar to 19 and sensors could also be used with this embodiment. It is understood that the number of containment areas or buckets can be varied to process the requisite number of collections and that four or six containment areas are just exemplary.

Figure 3:
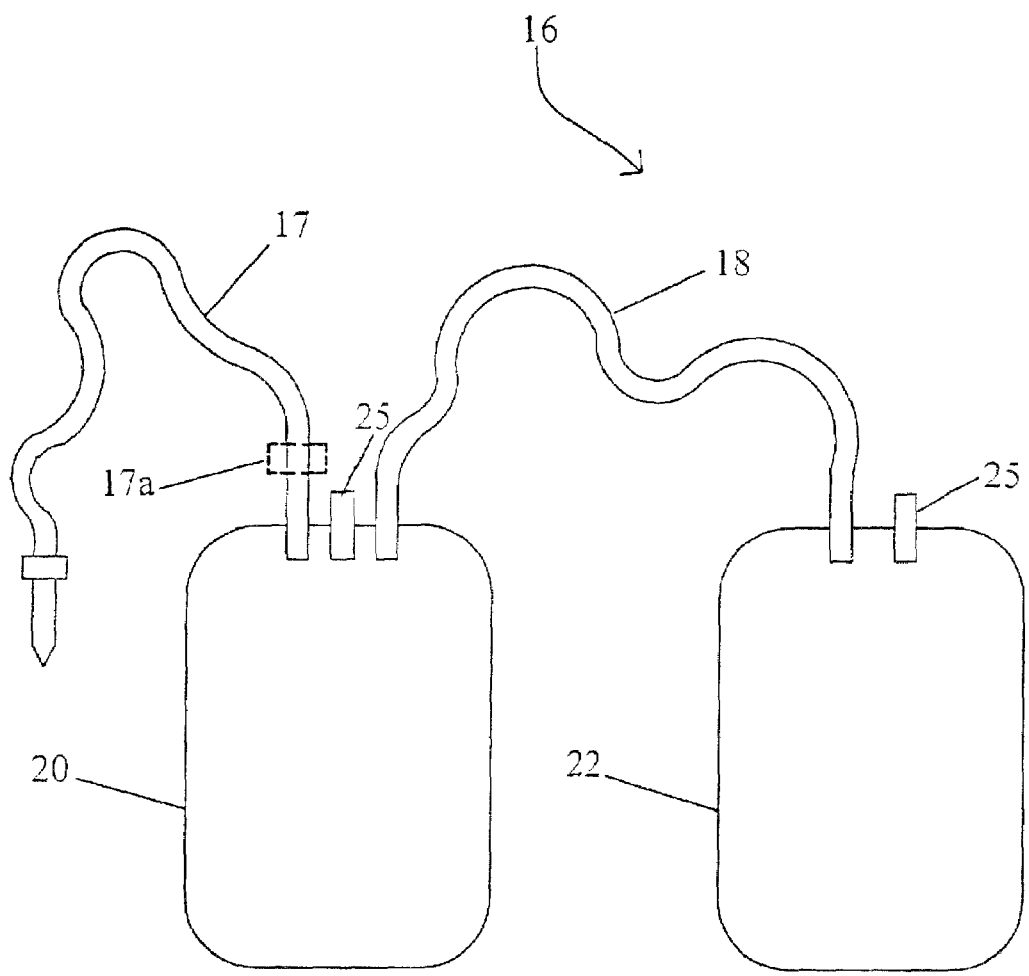
FIG. 3 is a view of a first embodiment of a tubing and bag system according to the present invention.

As introduced in FIG. 1 above system 10 uses a tubing and bag system 16 which is shown in more detail in FIG. 3. As shown here, this bag system 16 includes two bags 20 and 22 each connected to each other through respective tubing lines 18. An initial collection line needle assembly 17 is also shown, although this may be removed by RF sealing and cutting at or near point 17a. After separation and transfer of plasma to bag 22, the plasma bag 22 may be sealed off from and cut and/or removed from bag 20 using, in one example, a radio frequency (RF) heat sealing device (not shown) as understood. This removal may be made at a portion of tubing line 18 near bag 22. The remainder of tubing 18 may also be removed from bag 20 as well. As will be described, if more than two bags are used, similar disconnections of such bags (not shown) and/or at their respective tubing lines may occur, though occurring after the centrifugal separation process.

In one possible embodiment, wherein a rigid container is used instead of bags 20, 22, such rigid container could also include an air vent structure (not shown) to either allow air to enter the container as separated phases of fluid are removed or allow air to leave the container. Microbiological filters (0.2 micron size and the like) may be used in or with vents (not shown) to maintain sterility. Each of the bags or containers may also include a port structure 25 (see bags 20 and 22 in FIG. 3) for, inter alia, subsequent access to the collected separated components which may be disposed therein. Other structures and/or uses therefor may be disposed on or in or for each bag or container as may be understood and/or desired in the art.

Note, construction of the bag and tubing line parts of system 16 may take many understood forms and use many known materials, including flexible materials. For example, RF or heat welded sheet plastic (e.g. plasticized PVC bags and extruded flexible tubing lines can be used, as may blow-molded or other types of containers (e.g., glass, plastics) and lines. Even vessel 26 (see FIGS. 9-10, described below) may be formed from RF or heat welded flexible plastic sheets or may be blow-molded or otherwise formed as a rigid container and thus in a non-flexible form.

Returning now to FIGS. 1 and 2 and including further reference to FIGS. 5-8 a general description of the blood and blood component flow paths, when device 10 is used for the separation of blood into components, will now be described. First, note that the flow paths are within bag and tubing set 16 as disposed within rotor 12 (see FIGS. 5-8); however, in some embodiments, a bag set may not be used and the respective flows may simply be in sealed channels and pockets of rotor 12 (thus, channels may be formed in a rotor part and correspond to tubings such as tubings 18, whereas the pockets would correspond to the buckets or areas 15). In any case, as generally shown, particularly in FIGS. 1 and 2, for the tubing line or channel flow paths, whole blood is collected from the donor via line 17 and disposed in the bag 20 (as is generally known in the art) perhaps while bag 20 is in, but before disposition of bag 20 in the centrifuge device 10. If before disposition in rotor 12, then bag 20 may be disposed in a separate container (not shown) or hung from a hook or placed on a scale (not shown) as understood in the art for collection of whole blood from a donor, or in a fashion which allows for gravity drainage thereinto. A temporary outflow stopper as by a frangible connection or a slide or roller clamp (not shown) may be used in line 18 during collection in bag 20. Shown in FIG. 3 are the other tubing lines of tubing system 16 which provide the inlet and exit flows to and from the bag 20 as this will be disposed in the centrifuge rotor 12 during subsequent centrifugation. Thus, during such centrifugation (and after disconnection from a donor) the whole blood will be restricted or not allowed to flow from bag 20 to the bag 22 through tubing line 18. However, after separation in bag 20, the separated blood components; in particular red blood cells (RBCs) and plasma, will be separated such that the plasma will flow through respective tubing lines 18 for collection in respective containers 22. The RBCs will remain in container 20 and plasma flowed through tubing line 18 for collection in container 22.

Note, shown schematically also in FIG. 8 are optional clamps or valves 19 disposed in or adjacent channels or tubing lines 18 and which may be used to ensure no flow conditions in channels or tubing lines until desired, as for example, until a sufficient rotational speed has been achieved. Heads 141 of assembly 14 may be used to occlude lines 18 until flow is desired. Optical sensors 99 are also shown schematically as these may be disposed in/on or relative to rotor 12 and tubings 18. Sensors 99 would sense when a different phase (darker vs. lighter, e.g.) would reach into tubing 18 and would provide a signal (using logic circuitry and/or a computer chip) which would be used (interpreted or the like) to or for closing the associated clamp valve 19. Other types of sensors or flow restrictors could also be used as described above.

Prior to and during centrifugation, the tubing lines 18 are disposed in corresponding channels particularly, at least races 142 formed in/on the rotor 12. Thus, the flows in and through the centrifuge unit 10 are as follows (with or without tubing lines, as introduced above). Whole blood from the donor now contained in bag 20 (or perhaps collected otherwise, e.g., directly into rotor 12 into a containment area/bucket without a bag 20) is initially placed in the composite fluid containment area or buckets 15 of the rotor 12. The empty plasma bags 22 are positioned in their respective collection buckets 15 as are the respective tubing lines 18 within their respective channels or races 142. While in the receiving/containment area or buckets 15, the blood is then exposed to centrifugal forces when rotor 12 is spinning (which the rotor 12 is made to do after the whole blood, in bag 20 is placed into or is otherwise resident within centrifuge unit 10). Note, the initial exposure of blood to the centrifugal forces is relative to the axis of rotation 45 (see FIG. 1 where axis 45 is shown as a central point indicating the perpendicularity thereof relative to the drawing sheet). Under the centrifugal forces of the spinning rotor 12, the blood and particularly the heavier phase component 92 (RBCs) thereof is moved to the periphery of the containment area 15 (see FIG. 6) and is thus generally moved into a generally abutting relationship with the bottom wall which defines the containment area 15.

After the separation, the cooperative rotation of pump assembly 14 with rotor 12 is stopped or varied so that rotor 12 can continue to rotate at a different RPM than the pump assembly. A continuous flow of a separated blood component, e.g., plasma, 91 will then be made to flow from the fluid receiving area 15 into the channel/tubing line 18. This blood component will then travel substantially inwardly radially to the pump head. This is shown schematically in FIG. 7 wherein flow arrows are provided to show the direction of flow throughout the centrifugation configuration therein. This first flow is indicated by flow arrow 30 (See FIG. 7) continuing from the bag 20 to the pump assembly 14 and then goes radially outwardly back to the containment/receiving area 15. First, it should be noted that when the centrifuge rotor 12 is spinning (again, as it will be whenever blood is disposed therein), this will impart centrifugal forces on the blood which will then separate it into two primary components; namely, red blood cells (RBCs) and plasma. The heavier RBCs will settle outwardly under these centrifugal forces, and will thus accumulate, against or adjacent the outer wall of containment area 15. This action is shown in detail in FIG. 6. The plasma is identified generally by the reference number 91 in FIGS. 6-8, and the RBCs are similarly identified generally by the reference number 92. Whole blood prior to separation is shown in FIG. 5 and identified by the numeral 90 therein.

At least one optical sensor working in combination with at least one valve 19 (see FIG. 8) retains the more dense phase within containment area 20. This yields a distinct advantage. First, after separation and thus formation of an interface (see FIGS. 6 and 7) the plasma is removed from the bag 20 by the pumping action of assembly 14. During this pumping step the plasma is removed from the top of the bag and the bag collapses downward with the removal of plasma volume.

Various methods can be used to control the collapse of the bag so that the bag does not fold on itself and thus allowing the interface to remain relatively stable and stationary. Also controlled collapse will prevent the more dense phase or RBCs from being trapped in crevices or folds of the bag and help prevent less than optimum separation. These include, but are not limited to, tenting or hanging the bag. It is also understood that other methods for retaining the shape of the bag for proper collapse can be used.

The interface should be controlled in bag 20, so that it remains either radially outwardly enough so that the separated plasma can be moved through the outlet channel (the post-pump portion of tubing 18) and into bag 22 without undesirably diluting the plasma product with buffy coat or the RBC product. The "buffy coat" blood component, as known in the art, generally rides on the interface. The buffy coat generally includes platelets and white blood cells therein. The interface remains controlled because the centrifugal field is maintained during pumping.

An alternative could involve capture of these buffy coat blood components which could prevent contamination of either of the RBC or particularly the plasma products as well as potentially being useful in further processing to capture platelets separated from buffy coat cells. White blood cells (WBCs) which are substantially captured by the buffy coat are particularly unwanted in RBC, plasma and platelet products. However, because centrifugal separation will less effectively separate WBCs from RBCs (or platelets), the WBCs are more likely to be addressed separately relative to the RBCs (or platelets) with a (pre- or) post-centrifugal processing and/or filtration. In other words, the present invention, like other centrifugal separation systems, will likely not sufficiently leukoreduce red blood cells. Rather, although the buffy coat including the WBCs will ride on the RBC layer, they will not likely be sufficiently separated from the RBCs here so as to produce a leukoreduced RBC product. However, the buffy coat including WBCs can be sufficiently centrifugally separated from the plasma product by the present invention so long as the interface is sufficiently controlled as taught herein.

Note, the buffy coat may be retained sufficiently in an optional vessel 26 (FIGS. 9 and 10) (particularly using the automatic optically sensed/activated shutoff feature) so that the buffy coat may be collected and further processed into component parts (such as platelets, e.g.) for further use in transfusion, inter alia. Thus, as with the previous embodiment of FIGS. 3-6, an optical sensor 199 appropriately positioned adjacent to the container 26, would sense when a distinctly colored substance (e.g., the buffy coat and/or RBCs) arrives at that point, at which time this sensed parameter can be used to signal for closure of a clamp, see, e.g., clamp 119, FIG. 9) to stop flow in the tubing line 18 and thereby capturing buffy coat in vessel 26, which also captures RBCs in bag 20 and plasma in bag 22.

One primary advantage of a system such as this is that the lighter phase component plasma 91 can be made to continuously flow from the collection area 15 while the blood components are still in the centrifugal force field, and blood components 91 and 92 thus remain continuously separated and/or remain continuously separating therein even during this continuous flow out of the bags 20 and into the respective collection areas or bags 22 of rotor 12.

Several other important advantages are achieved with a system such as that shown and described herein. A first such advantage is the elimination of numerous complex control elements which were often required in previous centrifugal separation systems. For example, the separate manual expressor required for traditional bucket separation process can be eliminated. Furthermore, no separate expressor fluid system is necessary. Also, the optical/valve interface control shown and described here eliminates the need for other feedback loop interface control elements including complex pump controls, for example. The present controls can also be substantially independent of the blood hematocrit (within normal ranges of donor hematocrit) and relative flow rates of the inlet and outlet fluids. This eliminates the need for complex flow rate calculations and pumps and pump controls therefor (i.e., eliminates computer calculations and multiple flow control pumps; in various conventional embodiments, multiple pumps, inlet and outlet, have been required to be maintained in dynamic control relationship with each other constantly by computer in order to provide proper interface control). Thus, at the least, no inflow pump is required here, and a separated blood component may instead be fed from the whole blood container 20 into the tubing line 18, and through optional vessel 26 by the cooperating forces of the spinning rotor 12 and the relatively stationary fluid roller pump 14. The lack of an inflow pump and closed, but batchwise/continuous process as well as the less complex rotational drive mechanism further eliminates the need for a rotating tubing loop. This serves to greatly reduce the quantities and sizes of the mechanical components (tubing loops in rotating loop systems often generally dictate the minimum mechanical element requirements and size). A closed batchwise system (no inflow pump) also eliminates any need for a rotating seal at the inlet connection of the inflow line to the separation device. This greatly reduces complexity and a large potential for operational failure. Also, the rotor and housing combination are easily made in a totally closed system which can be simply sterilized and can be completely disposable, or, as particularly in the case of rotor 12, reusable without sterilization particularly if used with completely closed, sterilized tubing bag systems 16 as described herein. The reduced mechanical and control complexities contribute to the disposability and/or reusability benefits as well.

One advantage of the instant invention is that more plasma can be collected or separated than by the traditional manual expression of the blood bag using a separate expressor apparatus after centrifugation. This allows more plasma to be available for various needs and allows the residue cell component to have less plasma.

A further advantage can be realized in the output product quality. Particularly, due to the suction action of the pump and bag collapse in the current invention the interface may be stable and non-moving during pumping and thus virtually all of the plasma is removed. Removal of the plasma under the g-forces of the centrifugal field helps maintain the stable interface. Also, a virtually constant maximum hematocrit may be obtained for all resultant red blood cell products because the presently described separation device may be operated within a range of revolutions per minute (RPMs) at which the product hematocrit does not substantially vary. For example, the present invention may be operated at high RPMs; speeds which are heretofore not usually achievable for various reasons (e.g., drive mechanism or tubing loop or rotating seal problems at such high speeds). And, at such speeds, virtually all RBCs will be separated out from the input whole blood, thus yielding an RBC product with the highest available hematocrit. Note, the highest available hematocrit is a number above 80% and less than 100% and which approaches a substantially constant asymptote which is in the area of approximately 90 or 95%. At speeds in the range of such high RPMs, the resulting hematocrit is virtually equivalent to the asymptotic maximum throughout that range. At much lower speeds (e.g., 3000 RPMs or below), the resulting hematocrit may significantly diverge from the asymptotic maximum. FIG. 8 shows the system at or near the end of a process such that the original whole blood bag 20 and the collection bag 22 are filled with respective high quality RBC and plasma products. In the FIG. 9 embodiment the same high quality is also achievable with little remaining in the vessel 26 except a desirable buffy coat product. Note, an appropriately sized chamber (not directly shown) to hold vessel 26 could assist in capturing only the buffy coat in a flexible vessel 26 and at a constant predetermined volume. Or, as a similar alternative, vessel 26 could be a non-flexible member of a particular pre-selected size and shape which could be used to maximize the buffy coat collection/retention therein and minimize the inappropriate dilution thereof with either plasma or RBCs.

Note, a further primary advantage is that a rotor 12 configuration with buckets 15 can be made in unique centrifuge machines, or can be retrofitted onto/into pre-existing currently available centrifuge machines, such as those commonly manufactured and distributed by Hitachi, Ltd. (Japan) or the Sorvall Corporation, a.k.a., Sorvall Products, L.P. (Newtown, Conn.) (see e.g., FIG. 2). Pump assembly 14 braking members (not shown) may also be retrofitted onto such pre-existing, currently available centrifuges as well.

Referring once again to FIG. 1, a few basic alternatives will now be addressed. First, it should be noted that the embodiments shown in FIGS. 1-8 may also provide for separation of other composite fluids capable of centrifugal separation. Indeed, other blood component products may be processed using this system. Thus, where the FIGS. 1-8 embodiment is generally directed to separating composite fluid in a container 20 into two primary components and then moving the lighter phase into the other container 22; this can be used for processing, e.g., washing glycerolized RBC products, or for removing pathogen reduction agents/solutions from blood components such as RBCs and/or platelets.

More specifically, in a pathogen reduction process, this two-bag system could be used first to separate whole blood into component products as described above; after which separate processes and/or machines could be used to add and/or activate (e.g., illuminate) pathogen reduction agents/ solutions (e.g., photosensitizer solutions) to the separated blood component products. Then, the systems of the present invention could be used again to centrifugally separate the pathogen reduction agents/solutions from the now-processed blood component product (RBCs or platelets). The RBCs or platelets would be a heavier phase product which would remain in the initial bag 20 while the lighter phase pathogen reduction agent/solution would be lighter and after centrifugal separation could then be pumped out of the initial bag 20 by pump assembly 14 into a secondary bag 22 via a tubing line 18.

Another basic alternative available with this invention involves the optional return of certain separated blood components back to the donor, rather than retaining these in the collection reservoirs 20, 22. An example embodiment for returning a quantity of either (or both) separated RBCs and/or separated plasma back to the donor is not shown in the drawings but may take place after centrifugation, collection and any further processing is completed. As such, a bag 20 containing separated RBCs and/or a bag 22 containing plasma may be removed from the rotor 12 and then treated, stored or otherwise dealt with in the ordinary course. Then, when reinfusion to the donor or transfusion to a patient is desired, an infusion line (not shown) may be connected to and through a port structure 25 in a fashion known in the art (using, e.g. a spike, needle or other sterile docking connection means). Then, when it may be desired to return a quantity of a separated component (RBCs or plasma) to the donor (or transfused to another patient), the desired component may then be allowed to flow out of its respective container 20 or 22 or the like, through its respective return/infusion line (not shown), back toward and into the donor or patient. Accomplishment of these particular flows may simply involve gravity drainage of the desired blood component from its collection/storage bag 20 or 22, and/or it may involve the use of one or more pumps which may be of the peristaltic type. Thus, respective pumps may be engaged with each return/infusion line (not shown) and then may be activated at a desired operational point to pump the desired separated blood component out of its reservoir and through the respective tubings, and back into the donor or patient.

Another alternative to the present invention is related to the pumping action. Although the rotation of the pump is stopped for relative movement between the rotor 12 and pump heads 141, it is understood that pumping could also be achieved after the rotor 12 ends its rotations. That is, the pump assembly 14 could be the rotating element during pumping.

One requisite for pumping is that there be relative movement between the pump race on the rotor and the pump head assembly. As described above, this can be achieved by altering the rotational speed of either the pump head assembly or pump race. For example, one of the pump heads or rotors could rotate at a different RPM than the other. Alternatively, a complete stoppage of one could be affected as described above.

Figure 11:
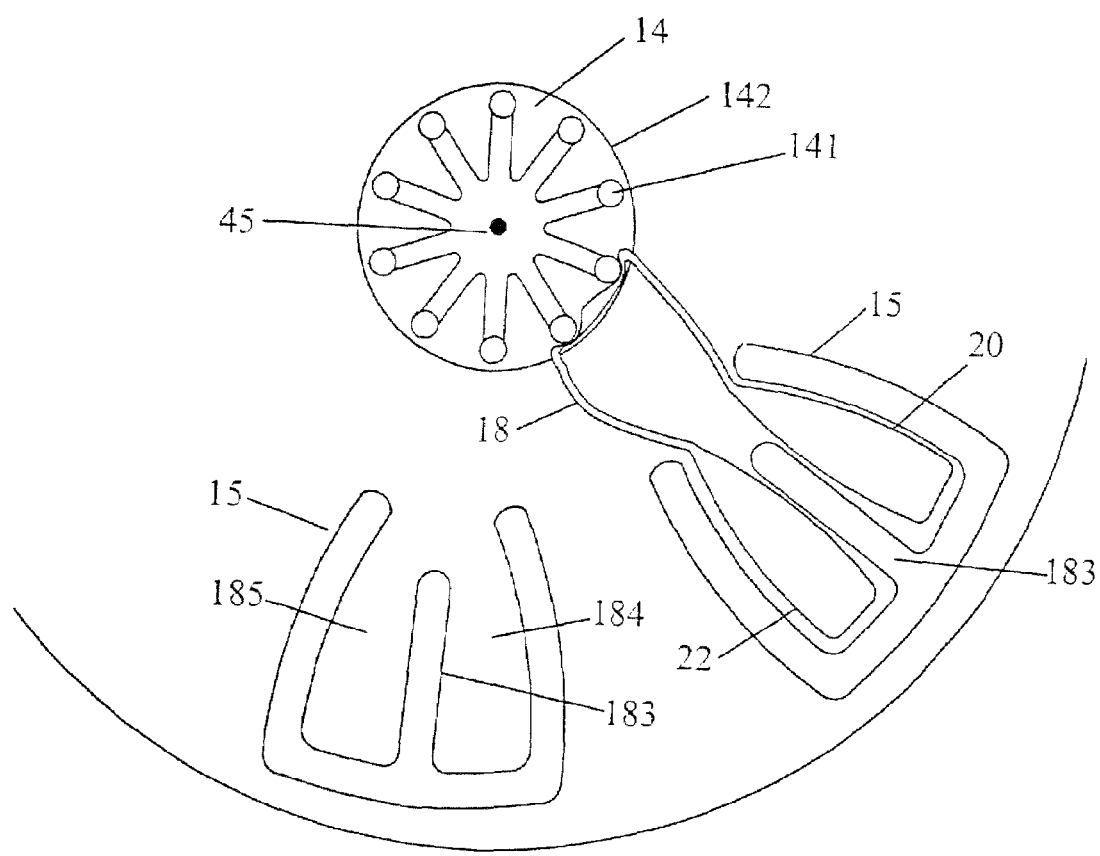
FIG. 11 is a plan view of an alternative rotor disposition and/or use according to the present invention.

Although a single containment area is described in the previous embodiments it is understood the containment areas could be partitioned by a wall such as 181 as shown in FIG. 11. Such a wall could also be used without a disposable where the fluid is moved through closed channels from one containment area to the other.

Another alternative using a centrally disposed pump assembly is an alternative where a ring-like separation bag is used. The pump assembly head could be used to pump through tubing connecting the ring-like separation bag to secondary bags. Also, it is contemplated that the roller head assembly can contact the separation bag itself. Thus the features of the instant invention can be applied to a number of disposables, not just the one described above.

Another alternative using the two bag systems 16 shown and described above (or other systems, see below) could be used to achieve platelet products and could be run as follows. First, after loading one or more whole blood products in respective bags 20 into respective buckets 15, the rotor 12 could be spun in a "soft spin"; not too high an RPM so that (as is known in the art), the whole blood in bags 20 can be separated into RBCs and a platelet rich plasma (PRP) product. Then, the rotor 12 can be slowed to an appropriate speed (RPMs) and the pump head 14 stopped or slowed to pump the platelet rich plasma to the second bag 22. Then, a hard spin can be made and platelets settled to the bottom of the second bag 22, and the RBCs packed tighter (higher hematocrit) in the first bag 20. Plasma thus further separated from the RBCs in bag 20 can be further transferred, if desired, to bag 22 to provide a higher hematocrit final RBC product in bag 20; and, the plasma in bag 22 can be removed therefrom using a conventional expressor or an expressor similar to 181 moveable about pivot 182 in bucket 15 (FIG. 13) into a third bag 23 (see FIGS. 12 and 13) through a line 18a. This third bag may be subsequently added to the two-bag set 16 or may be integral therewith (see FIGS. 12 and 13). As introduced above, this subsequent expression can be made to take place inside a bucket 15 (see FIG. 13) or outside, after careful removal and placement on a conventional expresser. A further alternative to the above two bag method to remove plasma from the PRP is that the rotation of the centrifuge or rotor 14 can be reversed to remove the plasma from bag 22 rather than using an off-line expresser.

Such a process provides several advantages. First, over conventional systems in which a PRP product is made in a standard bucket centrifuge, the separated PRP and RBC product must be removed from the bag by removing the bag from the centrifuge very carefully and placing this bag in a conventional expressor to remove the PRP from the separated product bag. Then, the expressed PRP product must be re-packed into a bucket, re-centrifuged, and then re-expressed. This process, that second spin and intermediate external expression with the inherent manual handling required thereby are avoided by the current invention. Both manual and multiple machine steps are avoided hereby. Note, manual handling in the conventional methods creates a significant amount of interface disruption and mixing of the centrifugally separated component products; this re-mixing being avoided with the present system. Also, and again, a higher crit (hematocrit) RBC product would also be obtained and more plasma product can be harvested.

Figure 12:
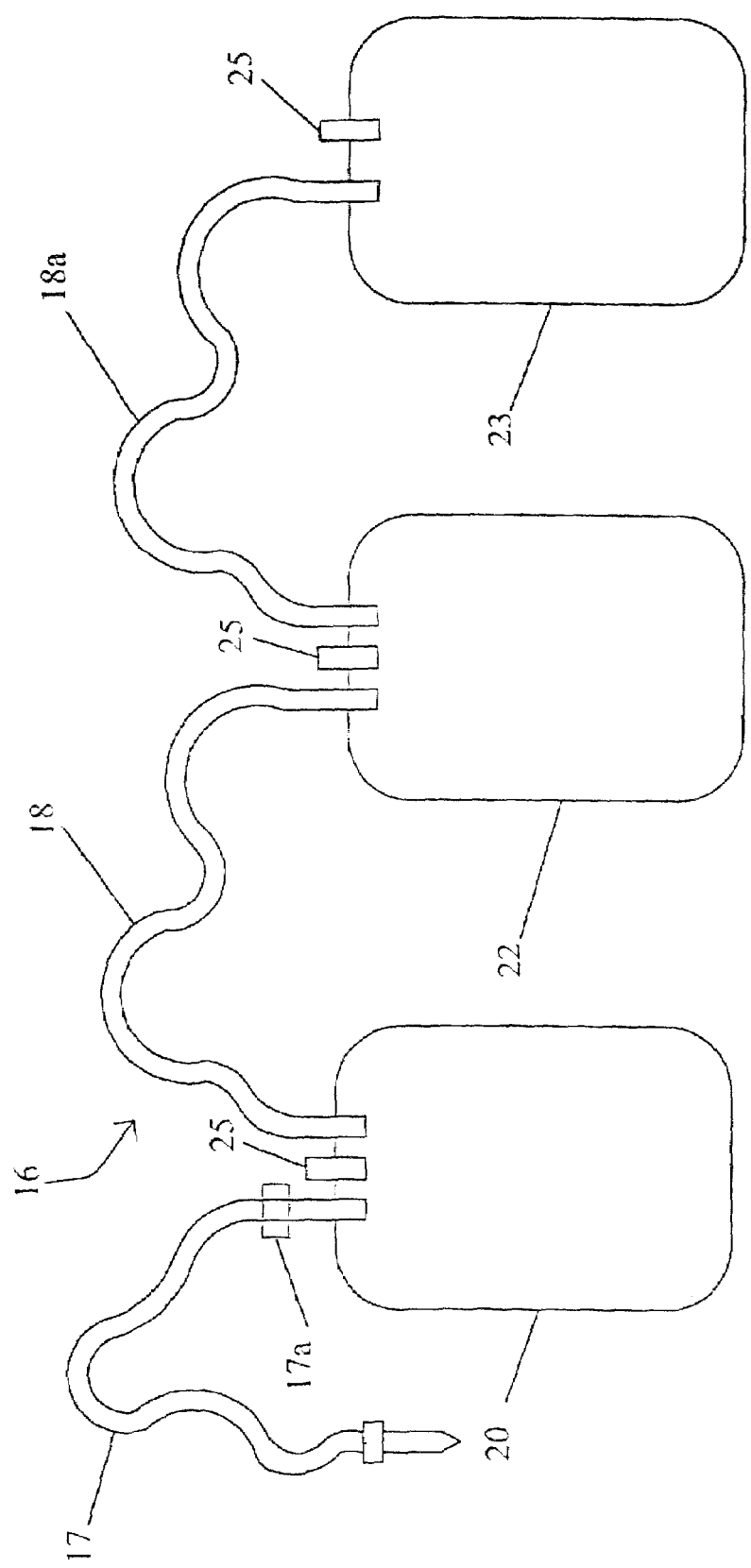
FIG. 12 is a plan view of another tubing and bag system alternative according to the present invention; and, FIG. 13 is a portional plan view of an alternative rotor disposition and/or use according to the present invention.
Figure 13:
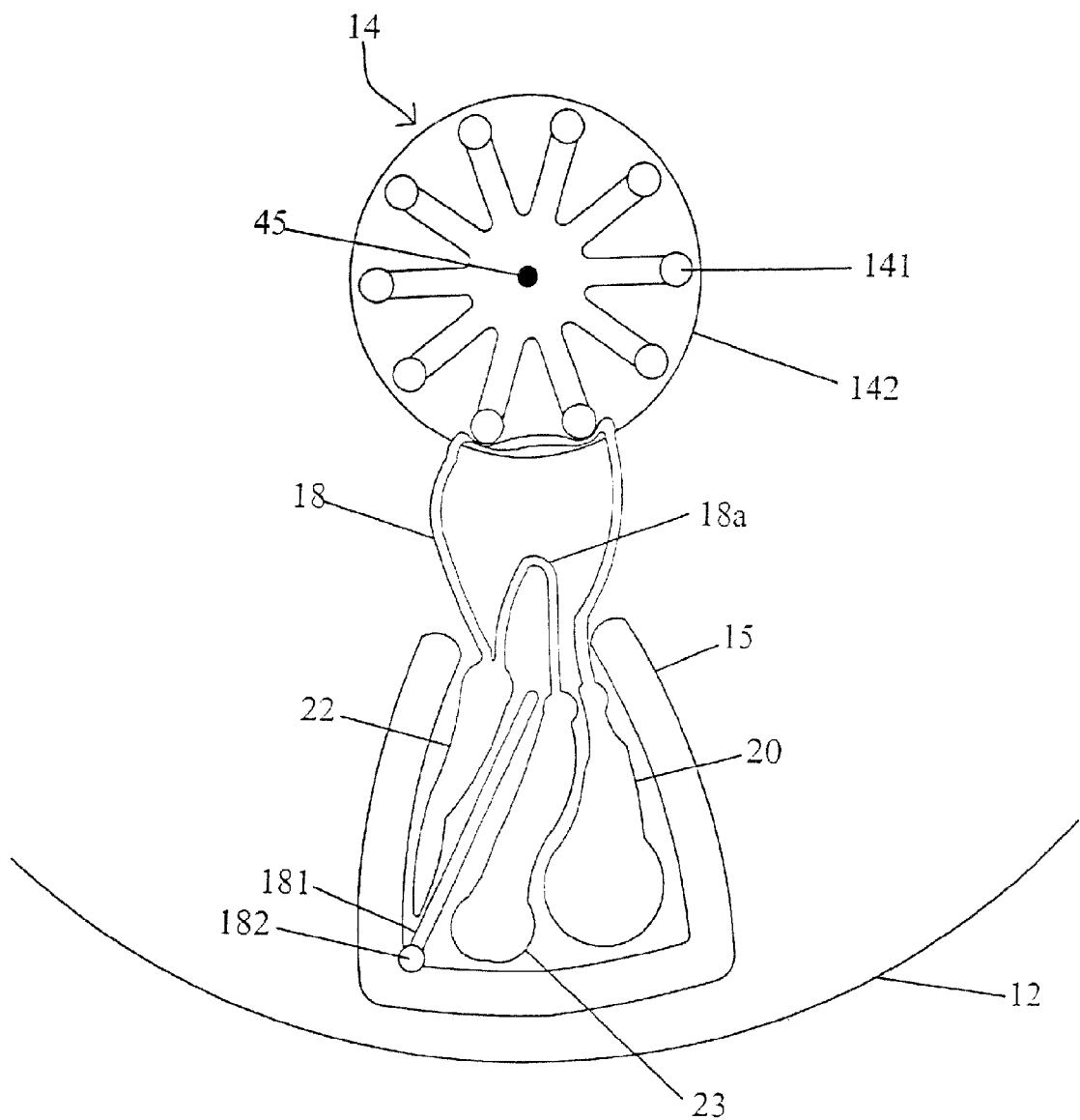

Turning now to a few more alternative embodiments, reference is first made to the plan view shown in FIG. 13. The primary distinction this centrifuge rotor 12 has over that shown, for example, in FIGS. 1-8, is that the separation buckets 15 have an expressor 181 moveable about 182 therein and a three bag set such as that shown in FIG. 12 is disposed therein. Nonetheless the functionally remains substantially the same in this embodiment as it was in the embodiment of FIGS. 1-8. A composite fluid is still separated in a primary bag 20, and from there a separated component is flowed out of the containment area, to each respective outlet or collection area or bags 22.

However, in further operation, this FIG. 13 embodiment works as described before, but is rotated again about a central axis 45 as shown in FIG. 1 for further separation of the component product in bag 22 after which the expressor 181 can be engaged to move the lightest phase component, e.g., plasma from bag 22 to bag 23. This expression can be made to take place during continued rotation of rotor 12, or after rotor 12 has been stopped. The movement of the expressor about 182 can be to a predetermined stop to provide a predetermined volume in bag 22.

Thus, either platelets or a buffy coat product can be captured inside the intermediate bag 22. A first soft spin and first movement of component from bag 20 to bag 22 may yield a PRP product in bag 22 followed by a second, harder spin resulting in a pelletized (or otherwise more packed) platelet product in bag 22. However, if the first spin is a hard spin, then the separation in bag 20 is into a platelet poor plasma (PPP), a buffy coat and a packed RBC product. In such a case, both the PPP and the buffy coat would need to be moved to the second bag. Forward flow is here first also caused and maintained by the engagement of the roller pump 14 as before. Then, a second hard spin can be used to separate the buffy coat from the PPP in the second bag and the PPP can be expressed to the third bag, thus capturing the buffy coat in the second bag 22. Note, though not shown, the PPP bag 23 could be connected by tubing line directly to the first bag 20 with the first movement of PPP pumped via roller pump assembly 14 thereto; followed by buffy coat expression into bag 22 as described.

A further alternative here for buffy coat-like processing takes note of the fact that the buffy coat is processed better when it rides on a bed of RBCs. Thus, prior to any centrifugation a small quantity of whole blood may be moved from the initial container 20 to the intermediate container 22 (e.g., via roller pump 14 and tubing line 18). Then processing can proceed as introduced above. The processor can be first a soft spin then transfer of the PRP from bag 20 to bag 22, then a hard spin where the platelets separate and yet rides on a small layer of RBCs in bag 22, followed by the expression of PPP from bag 22 into bag 23.

The completion portion of the centrifugation process provides for substantially (if not completely) all of the whole blood (or like component fluid) to be separated with bags 20 and 23 having been substantially filled with respective components, RBCs 91 and plasma 92, with a minute remainder of fluids (or a platelet or a buffy coat product) in the intermediate bag 22. Rotation of rotor 12 can then be stopped and bag set 16 removed therefrom. Tubing lines 20, 21 can then be heat sealed and/or cut to separate collection bags 20, 22 and 23 therefrom for subsequent storage processing and/or use in transfusion (as known in the art). Note, the centrifuge rotor may be equipped with clamps and/or RF welding devices (powered through slip rings) which may be activated to clamp and/or weld and/or cut the tubing lines inside the centrifuge to provide isolated product bags prior to removal by the operator. Note also that preliminary or subsequent processing (e.g., leukoreduction, filtration, viral reduction or storage solution addition) prior to storage or use of the separated components may also be desired, and such may be performed before or after completion of the centrifugation process.

A challenge in implementing the RBC/plasma separation device described hereinabove involves mechanization of the process. Situations often may dictate a preference for processing of more than one whole blood unit at a time. According to some embodiments of the present invention, the above rotors are designed to be accommodated on and or by a standard centrifuge machine such as those which typically accommodate more than one whole blood unit or bag 20 with its associated component collection bag(s) 22 (23). Such is provided by the embodiments hereof.

As introduced in the above-described embodiments, the single blood separation pathway of the initially described centrifugation configuration embodiments (see FIGS. 1-8 and 9-11, e.g.) can be divided into multiple, usually opposing flow pathways. For example, FIG. 1 shows the incorporation of six discrete processing areas 15, in/on one rotor 12 while FIG. 14 shows four. As the number of processing areas and/or as the, increases then larger driving centrifuge motor bases (not shown) will likely need to be used. Nonetheless, it appears that a multi-unit rotor such as rotor 12 of FIGS. 1-8 (or other quantity units from two up to perhaps eight, twelve, or even more units) may be made to replace the rotor of an existing bucket or cup centrifuge machine; such machines typically already being used in blood banks for blood component separation. Thus, existing drive machinery may be used to generate the forces desirable for separation and flow (e.g., high revolutions per minute (RPMs) and/or large g forces such as up to perhaps 5000 g's (5000×gravity), for an example). A limiting factor may be the vapor pressure of the fluid as this may be related to the relative head "height" presented by the distance of the fluid away from the center of rotation. That is, if the distance is too far for the particular fluid (and its characteristic "vapor pressure"), the pump may not be able to pump over the vapor pressure of the fluid and a sort of vapor lock, no-flow condition could result. One option for correcting this problem is to use lower RPMs. Another option is to reduce head "height" of the suction part of tubing 18.

Among various advantages of these embodiments, one may be found in the tubing and bag sets 16 which may be used herewith as shown, e.g., in FIGS. 3 and 12. The tubing and bag sets 16 of FIGS. 3 and 12 differ very little from each other. For example, there are two or three primary bags; a composite fluid/whole blood bag 20 and one or two separated component bags 22 and/or 23 (RBCs collected in bag 20, and plasma in bag 22 or 23 and platelets or buffy coat collected in the other secondary bag 23 or 22) with associated tubing line connections 18 and 18*a* emanating therefrom. These bags are also made in the same fashion and from the same types of materials as the other conventional bags. (Note, as introduced above, a bag was suggested as an alternative vessel 26 for the embodiment of FIG. 10, as well). Nevertheless, these bags may be shorter (or longer) and/or perhaps wider (or thinner) and/or may have less (or more) volume than any of the other bags, depending primarily on the composite fluids to be separated and the relative components resulting therefrom, and/or the rotor configurations chosen, e.g., the length and width of the separation bucket 15 or otherwise as may be desired. Bottles or containers of other types may also be alternatively used herein with air vents being included in hard wall containers for proper fluid flow.

Figure 15:
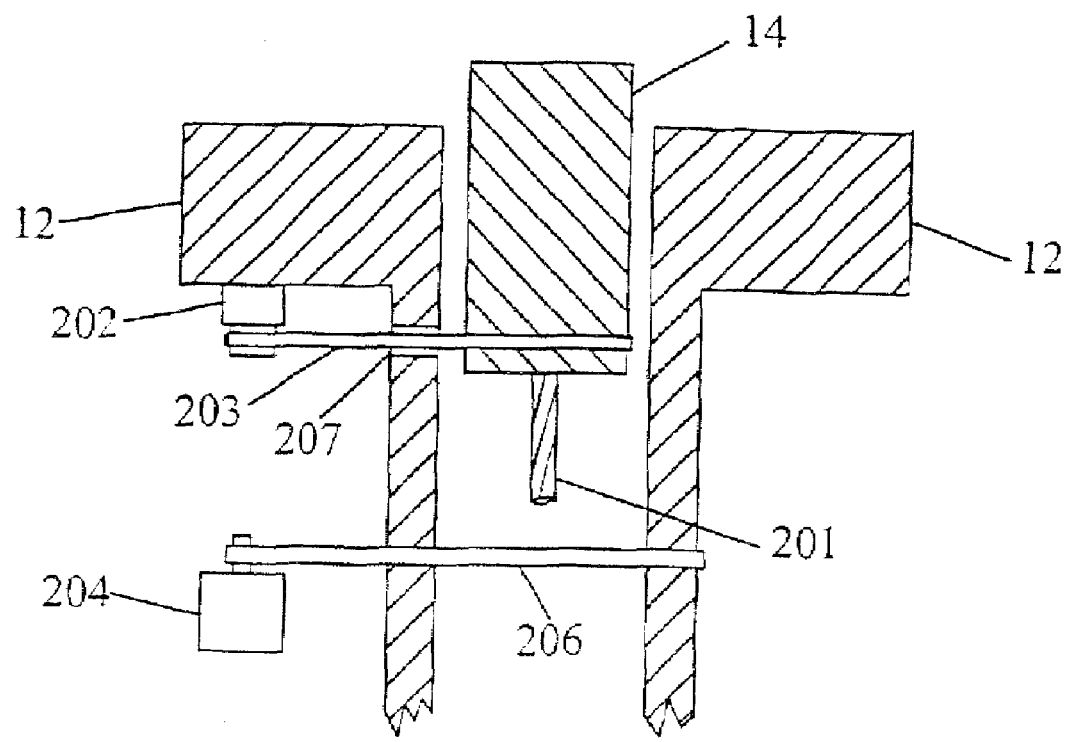
FIG. 15 is a partial cross-sectional view showing a generator mounted on the rotor.
Figure 16:
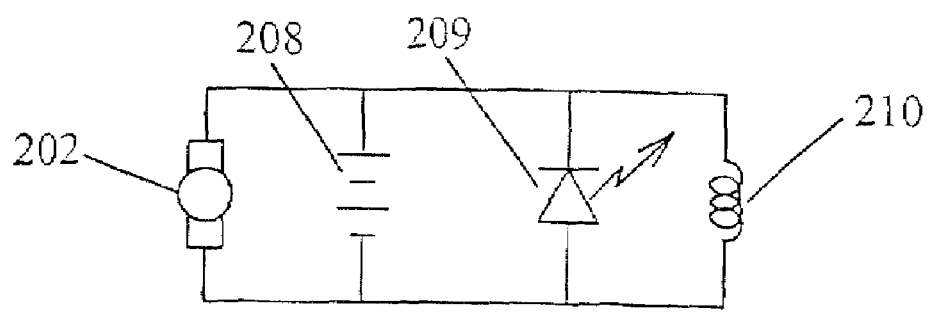
FIG. 16 represents an electric circuit attached to the generator of FIG. 15.

FIGS. 15 and 16 illustrate an optional feature to the centrifuge configuration described above. FIG. 15 is a partial cross-sectional view showing rotor 12 and pump assembly 14 as described above. Element 201 represents a brake or other apparatus or mechanism for stopping pump assembly 14 from rotating with rotor 12, also as described above. The brake would be engaged during the pumping mode to stop the rotation of pump assembly 14. A generator is shown at 202 attached to rotor 12. Although only one generator 202 is shown it is understood that several could be mounted on rotor 12. A belt 203 is shown passing through slot 207 on rotor 12 to couple the generator 202 to pump assembly 14.

The main drive for rotor 12 is also shown in FIG. 15. This drive consists of motor 204 coupled to rotor 12 by drive belt 206.

In operation motor 204 will drive both rotor 12 and pump assembly 14 rotating therewith during the separation portion of the above-described processes. However, upon application of brake or mechanism 201, pump assembly 14 will stop rotation while rotor 12 continues to rotate, possibly at a lower RPM. This relative movement between pump assembly 14 and rotor 12 will turn the generator 202 using belt 203 or other drive mechanism. Although a motor belt arrangement is described above, it is recognized that other known drive mechanisms could be used to provide the energy generation. For example, a gear system could alternatively be used.

FIG. 16 illustrates possible uses of the electricity generated by generator 22. For example, such electricity could power one or several light emitting devices shown at 209 for an optical sensor. It could also, alternatively or cumulatively power one or more solenoids 210 for valving of tubing line 18.

Alternatively the generator could charge a battery 208 for subsequent use. It is further understood that there may be other uses for the centrifuge configuration 10 for any electrically generated other than those described above. Also, battery 208 can also be mounted on rotor 12 and connected to the desired electrical device using elements by known connections.

It is understood that a battery 208 could be mounted on rotor 12 without generator 202 and that such battery can be of the replaceable or the rechargeable type. Such battery could provide the necessary electricity needed for the desired electrical devices.

Other variations (not shown) are also possible including numerous options such as, but not limited to, processing unit quantities and/or structural placements of various containment and/or collection areas and/or channels on the respective rotors and/or relative to each other. Methodology options also abound. Hence, these and various further modifications, adaptations and variations of the structure and methodology of the present invention will become apparent to those skilled in the art without departing from the scope or spirit of the present invention. It is intended that the present invention cover all such modifications, adaptations and variations as limited only by the scope of the following claims and their equivalents.

What is claimed is:

1. A centrifuge and disposable combination for centrifugally separating a composite fluid into component parts thereof comprising
   a rotor comprising
      a plurality of composite fluid containment/separation areas, each fluid containment/separation area comprising
         a composite fluid area;
         a component collection area; and
         a fluid channel;
   a roller pump mechanism disposed concentrically with the rotor;
   a plurality of disposables, each disposable comprising
      a composite fluid bag in one of the composite fluid areas;
      a component collection bag in one of the component collection areas; and
      tubing in one of the fluid channels and connected to the composite fluid bag and the component collection bag of the disposable;
   a motor for rotating the rotor wherein the roller pump mechanism engages the tubing of each disposable for rotating the roller pump mechanism with the rotor during separation of the composite fluid.

2. The combination of claim 1 further comprising a stopping mechanism to stop the rotation of the roller pump mechanism with the rotor wherein a separated component is pumped through the tubing of each disposable to the component collection bag.

3. The combination of claim 2 wherein the stopping mechanism is a brake to stop the rotation of the roller pump mechanism while the rotor continues to rotate.

4. The combination of claim 2 wherein the stopping mechanism changes the speed of rotation of the roller pump mechanism relative to the rotor to stop the rotation of the pump mechanism with the rotor.

5. A centrifugation configuration for centrifugally separating a composite fluid into component parts thereof, said configuration comprising
   a rotor comprising
      a plurality of fluid containment/separation areas, each fluid containment/separation area comprising
         a composite fluid area; and
         a component collection area;
   a roller pump mechanism disposed concentrically with the rotor;
   a plurality of fluid channels wherein each fluid channel is disposed in fluid communication with a composite fluid area and disposed in fluid communication with a component collection area; whereby each fluid channel is adapted to engage said roller pump mechanism so as to provide a fluid pumping relationship for moving a respective separated component from each composite fluid area to each component collection area through each fluid channel.

6. A centrifugation configuration according to claim 5 in which each composite fluid area comprises a first bag; and each component collection area comprises a second bag.

7. A centrifugation configuration according to claim 5 in which said roller pump mechanism is operable to move with said rotor when not engaged in a pumping operation and alternately operable to be disengaged from said rotor when operating in a pumping operation.

8. A centrifugation configuration according to claim 5 wherein the composite fluid to be separated is whole blood and the whole blood is separated into first and second components, namely, a heavier phase component and a lighter phase component.

9. A centrifugation configuration according to claim 8 wherein the heavier phase component includes red blood cells and the lighter phase component includes plasma.

10. The centrifuge configuration of claim 8 wherein said rotor further comprises at least one sensor for sensing the flow of heavier phase component from each composite fluid area to said fluid channel and for producing a signal in response thereto.

11. The centrifuge configuration of claim 10 wherein said rotor further comprises at least one clamp for receiving the signal from said sensor and for clamping at least one fluid channel in response thereto.

12. The centrifuge configuration of claim 11 wherein said rotor further comprises a battery mounted on said rotor for providing electricity to said clamp.

13. The centrifuge configuration of claim 10 wherein said rotor further comprises a generator mounted on said rotor to provide electricity to said sensor.

14. A centrifugation configuration according to claim 5 wherein the composite fluid to be separated is whole blood and the whole blood is separated into a heavier phase red blood cell component and a lighter phase plasma component and an intermediate phase platelet component.

15. A centrifugation configuration according to claim 5 wherein each composite fluid area comprises
  a disposable composite fluid container;
wherein each component collection area comprises
  a component collection container;
wherein each fluid channel comprises
  a tubing line; whereby each composite fluid container is connected to one of said component collection containers by said tubing line to form a connected disposable system, and whereby each tubing line is adapted to be engaged with said roller pump mechanism.

16. A centrifugation configuration according to claim 15 wherein the disposable system further comprises a second component container; and whereby said second component container is connected to said composite fluid container by said tubing line.

17. The centrifugation configuration of claim 5 further comprising a centrifugal drive motor base wherein said rotor is disposed in an operable rotor-driving position on said centrifugal drive motor base.

18. The centrifugation configuration of claim 17 wherein said roller pump mechanism is engaged with said centrifugal drive motor base during a separation stage, and further comprising a brake for disengaging said roller pump mechanism from said centrifugal drive motor base during a pumping operation.

19. A centrifugation configuration according to claim 18 in which said roller pump mechanism is operable to move with said rotor when not engaged in a pumping operation and alternately operable to be not engaged with said rotor when operating in a pumping operation.

20. The centrifugation configuration of claim 17 wherein said roller pump mechanism is engaged with said centrifugal drive motor base during a separation stage to rotate with said rotor and further comprising a mechanism for changing the speed of one of said rotor or said roller pump mechanism so that said roller pump mechanism and rotor have relative motion with respect to the other during a pumping operation.

21. The centrifuge configuration of claim 5 further comprising
  a plurality of buckets, each bucket containing one of said composite fluid containment/separation areas wherein each bucket comprises
    a wall separating said bucket into said composite fluid area and said component collection area.

22. The centrifuge configuration of claim 5 further comprising
  a plurality of buckets, each bucket containing one of said composite fluid containment/separation area; and
  a moveable expresser in each said bucket.

23. The centrifugation configuration of claim 5 wherein the rotor comprises a pump raceway for receiving each fluid channel and the roller pump mechanism further comprises a roller adapted to engage each fluid channel.

24. A centrifuge for separating a blood composite fluid into components comprising
  a rotor comprising
    a plurality of separation areas fixedly mounted thereon, wherein each separation area comprises
      a blood composite fluid area; and
      an associated component collection area; and
    a roller pump assembly cooperating with the rotor and adapted to pump separated components from each blood composite fluid area to each associated component collection area.

* * * * *